(12) United States Patent
Shea et al.

(10) Patent No.: US 8,173,618 B2
(45) Date of Patent: May 8, 2012

(54) FORMULATIONS FOR REDUCING NEURONAL DEGENERATION

(75) Inventors: Thomas B. Shea, Billerica, MA (US); Robert J. Nicolosi, Tyngsborough, MA (US); Eugene Rogers, Tyngsboro, MA (US)

(73) Assignee: University of Massachusetts, Boston, MA (US)

( * ) Notice: Subject to any disclaimer, the term of this patent is extended or adjusted under 35 U.S.C. 154(b) by 1642 days.

(21) Appl. No.: 10/898,393

(22) Filed: Jul. 23, 2004

(65) Prior Publication Data

US 2005/0043312 A1    Feb. 24, 2005

Related U.S. Application Data

(60) Provisional application No. 60/490,339, filed on Jul. 25, 2003.

(51) Int. Cl.
| | | |
|---|---|---|
| A61K 31/70 | (2006.01) | |
| A61K 31/52 | (2006.01) | |
| A61K 31/195 | (2006.01) | |
| A61K 31/50 | (2006.01) | |
| A61K 31/495 | (2006.01) | |
| A61K 31/22 | (2006.01) | |
| A61K 31/355 | (2006.01) | |

(52) U.S. Cl. ........... 514/46; 514/263.23; 514/562; 514/249; 514/458; 514/546; 514/547

(58) Field of Classification Search ............ 514/46, 514/263.3, 303, 562
See application file for complete search history.

(56) References Cited

U.S. PATENT DOCUMENTS

| | | | |
|---|---|---|---|
| 3,810,994 | A | 5/1974 | Wiegand |
| 4,255,449 | A | 3/1981 | Cavazza |
| 4,268,524 | A | 5/1981 | Cavazza |
| 4,751,242 | A | 6/1988 | Calvani et al. |
| 4,940,658 | A | 7/1990 | Allen et al. |
| 4,945,083 | A | 7/1990 | Jansen, Jr. |
| 4,968,719 | A | 11/1990 | Brevetti |
| 5,043,355 | A | 8/1991 | Cavazza |
| 5,192,805 | A | 3/1993 | Cavazza |
| 5,364,845 | A | 11/1994 | Henderson |
| 5,563,126 | A | 10/1996 | Allen et al. |
| 5,587,363 | A | 12/1996 | Henderson |
| 5,753,703 | A | 5/1998 | Cavazza et al. |
| 5,795,873 | A | 8/1998 | Allen |
| 5,916,912 | A | 6/1999 | Ames et al. |
| 5,958,886 | A | 9/1999 | Carter et al. |
| 5,997,915 | A | 12/1999 | Bailey et al. |
| 6,008,221 | A  * | 12/1999 | Smith et al. ............ 514/250 |
| 6,011,040 | A | 1/2000 | Muller et al. |
| 6,020,139 | A | 2/2000 | Schwartz et al. |
| 6,037,373 | A | 3/2000 | De Simone |
| 6,080,788 | A | 6/2000 | Sole et al. |
| 6,207,651 | B1 | 3/2001 | Allen et al. |
| 6,254,904 | B1 | 7/2001 | Bailey |
| 6,297,224 | B1 | 10/2001 | Allen et al. |
| 6,335,021 | B1 | 1/2002 | Cavazza |
| 6,335,361 | B1 | 1/2002 | Hamilton |
| 6,368,617 | B1 | 4/2002 | Hastings et al. |
| 6,369,058 | B1 | 4/2002 | Hussain et al. |
| 6,479,069 | B1 | 11/2002 | Hamilton |
| 6,528,496 | B1 | 3/2003 | Allen et al. |
| 6,544,547 | B2 | 4/2003 | Hageman |
| 6,562,869 | B1 | 5/2003 | Hamilton et al. |
| 6,565,876 | B1 | 5/2003 | Cavazza |
| 6,589,555 | B2 | 7/2003 | Pandya |
| 6,596,701 | B1 | 7/2003 | Schwartz et al. |
| 6,673,837 | B2 | 1/2004 | Fassi |
| 6,712,802 | B1 | 3/2004 | Cairns et al. |
| 6,733,797 | B1 | 5/2004 | Summers |
| 6,746,678 | B1 | 6/2004 | Shapiro |
| 6,784,209 | B1 | 8/2004 | Gardiner et al. |
| 6,822,002 | B1 | 11/2004 | Arduini |
| 6,964,969 | B2 | 11/2005 | McCleary |
| 7,049,321 | B2 | 5/2006 | Fisher et al. |
| 7,211,571 | B2 | 5/2007 | Pola |
| 2003/0119904 | A1 | 6/2003 | Fassi |
| 2005/0043312 | A1 | 2/2005 | Shea et al. |
| 2005/0107338 | A1 | 5/2005 | Seidman |
| 2006/0004095 | A1 | 1/2006 | Calvani et al. |
| 2006/0134147 | A1 | 6/2006 | Kalafsky |
| 2007/0213408 | A1 | 9/2007 | Calvani et al. |

FOREIGN PATENT DOCUMENTS

CA     2291959     6/2001

(Continued)

OTHER PUBLICATIONS

Grundman, "Vitamin E and Alzheimer disease: the basis for additional clinical trials" Am. J. Nutr. 2002; 71(suppl): pp. 630S-636S.*
Ho et al., "Folate deprivation induces neurodegeneration: roles of oxidative stress and increased homocysteine" Neurobiology of Disease, 14 (2003), pp. 32-42.*
Chiang et al., "S-Adenosyl-Lhomocysteine Hydrolase: Analogues of S-Adenosyl-L-homocysteine as Potential Inhibitors" Molecular PHarmacology, 1977, 13, pp. 939-947.*
Blom, Henk J. , "Consequences of homocysteine export and oxidation in the vascular system," Semin. Thromb. Hemost. 26(3):227-32 (2000).
Bottiglieri et al., "Cerebrospinal fluid S-adenosylmethionine in depression and dementia: effects of treatment with parenteral and oral S-adenosylmethionine," J. Neurol. Neurosurg. Psychiatry, 53(12): 1096-1098 (Dec. 1990).
Bottiglieri et al., "S-adenosylmethionine levels in psychiatric and neurological disorders: a review," Acta. Neurol. Scand.: Supplement, 154:19-26 (1994).
Bottiglieri et al., "The clinical potential of ademethionine (S-adenosylmethionine) in neurological disorders," Drugs, 48(2):137-152 (Aug. 1994).

(Continued)

Primary Examiner — Sreeni Padmanabhan
Assistant Examiner — Jody Karol
(74) Attorney, Agent, or Firm — Nelson Mullins Riley & Scarborough LLP; Debra J. Milasincic, Esq.; Brianna M. Erickson

(57) ABSTRACT

Nutriceutical and pharmaceutical formulations for treating neurodegenerative disorders such as Alzheimer's disease are provided. Nutriceutical formulations include two or more of folate, vitamin E, and acetyl-L-carnitine (ALCAR). Pharmaceutical formulations include two or more of 3-deaza-adenosine (DZA), N-acetyl-L-cysteine (NAC), and S-adenosylmethionine (SAM).

11 Claims, 12 Drawing Sheets

FOREIGN PATENT DOCUMENTS

| | | | |
|---|---|---|---|
| DE | 19824346 A1 | | 12/1999 |
| EP | 0516594 A1 | | 12/1992 |
| EP | 808626 A1 | * | 11/1997 |
| WO | WO 0232434 A1 | * | 4/2002 |

OTHER PUBLICATIONS

Bretsky et al., "Evidence for an interaction between apolipoprotein E genotype, gender, and Alzheimer disease," Alzheimer Dis. Assoc. Disord. 13(4):216-21 (1999).

Brooks et al., "Acetyl L-carnitine slows decline in younger patients with Alzheimer's disease: a reanalysis of a double-blind, placebo-controlled study using the trilinear approach," Int. Psychogeriatr. 10(2):193-203 (1998).

Christensen et al., "Homocysteine export from cells cultured in the presence of physiological or superfluous levels of methionine: methionine loading of non-transformed, transformed, proliferating, and quiescent cells in culture," J. Cell. Physiol. 146(1):52-62 (1991).

Cloughesy and Black, "Pharmacological blood-brain barrier modification for selective drug delivery," J. Neurooncol. 26(2):125-32 (1995).

Dringen and Hamprecht, "N-acetylcysteine, but not methionine or 2-oxothiazolidine-4-carboxylate, serves as cysteine donor for the synthesis of glutathione in cultured neurons derived from embryonal rat brain," Neurosci. Lett. 259(2):79-82 (1999).

Ekinci et al., "β-amyloid-induced calcium influx induces apoptosis in culture by oxidative stress rather than tau phosphorylation," Brain Res. Mol. Brain Res., 76(2):389-395 (Mar. 2000).

Ekinci et al., "β-amyloid-induced tau phosphorylation does not correlate with degeneration in cultured neurons," J. Alzeheimer's Dis., 2(1):7-15 (Mar. 2000).

Endresen et al., "Apoptosis and transmethylation metabolites in HL-60 cells," J. Pharmacol. Exp. Ther. 278(3):1318-24 (1996).

Fiskerstrand et al., "Folate depletion induced by methotrexate affects methionine synthase activity and its susceptibility to inactivation by nitrous oxide," J. Pharmacol. Exp. Ther. 282(3):1305-11 (1997).

Hatanaka et al., "A role of peroxides in Ca2+ ionophore-induced apoptosis in cultured rat cortical neurons," Biochem. Biophys. Res. Commun. 227(2):513-8 (1996).

Holcomb et al., "Behavioral changes in transgenic mice expressing both amyloid precursor protein and presenilin-1 mutations: lack of association with amyloid deposits," Behav. Genet. 29(3):177-85 (1999).

Huang et al., "Differential gene expression of livers from ApoE deficient mice," Life Sciences 68:19-28 (2000).

Jeong et al., "3-deazaadenosine, a S-adenosylhomocysteine hydrolase inhibitor, has dual effects on NF-kappaB regulation. Inhibition of NF-kappaB transcriptional activity and promotion of IkappaBalpha degradation," J. Biol. Chem. 274(27):18981-8 (1999).

Kennedy et al., "Elevated S-adenosylhomocysteine in Alzheimer brain; influence on methyltransferases and cognitive function," J. Neural Transm. 111:547-567 (2004).

Lovell et al., "Decreased glutathione transferase activity in brain and ventricular fluid in Alzheimer's disease," Neurology, 51:1562-1566 (1998).

Lucock et al., "The influence of dietary folate and methionine on the metabolic disposition of endotoxic homocysteine," Biochem. Mol. Med. 59(2):104-11 (1996).

Mattson et al., "Folate and homocysteine metabolism in neural plasticity and neurodegenerative disorders," Trends Neurosci. 26(3):137-146 (2003).

Mischoulon et al., "Role of S-adenosyl-L-methionine in the treatment of depression a review of the evidence," Am. J. Clin. Nutr., 76(suppl.):1585-1161S (2002).

Olivieri et al., "N-acetyl-L-cysteine protects SHSY5Y neuroblastoma cells from oxidative stress and cell cytotoxicity: effects on beta-amyloid secretion and tau phosphorylation," J. Neurochem. 76(1):224-33 (2001).

Ou et al., "The role of intracellular glutathione in methylmercury-induced toxicity in embryonic neuronal cells," Neurotoxicology 20(5):793-804 (1999).

Parihar et al., "Alzheimer's disease pathogenesis and therapeutic interventions," Journal of Clinical Neuroscience, 11(5):456-467 (2004).

Ramassamy et al., "Impact of apoE deficiency on oxidative insults and antioxidant levels in the brain," Brain Res. Mol. Brain Res. 86(1-2):76-83 (2001).

Ramassamy et al., "Oxidative damage and protection by antioxidants in the frontal cortex of Alzheimer's disease is related to the apolipoprotein E genotype," Free Radic. Biol. Med. 27(5-6):544-53 (1999).

Rimon et al., "Increased surface phosphatidylserine is an early marker of neuronal apoptosis," J. Neurosci. Res. 48(6):563-70 (1997).

Schulz et al., "Glutathione, oxidative stress and neurodegeneration," Eur. J. Biochem. 267:4904-4911 (2000).

Scorziello et al., "Acetyl-L-Carnitine Arginine Amide Prevents β 25-35-Induced Neurotoxicity in Cerebellar Granule Cells," Neurochemical Research, vol. 22, No. 3:257-265 (1997).

Shea and Rogers, "Folate quenches oxidative damage in brains of apolipoprotein E-deficient mice: augmentation by vitamin E," Brain Res. Mol. Brain Res. 108(1-2):1-6 (2002).

Shea et al., "Apolipoprotein E deficiency promotes increased oxidative stress and compensatory increases in antioxidants in brain tissue," Free Radic. Biol. Med. 33(8):1115-20 (2002).

Shea et al., "Efficacy of vitamin E, phosphatidyl choline, and pyruvate on buffering neuronal degeneration and oxidative stress in cultured cortical neurons and in central nervous tissue of apolipoprotein E-deficient mice," Free Radic. Biol. Med. 33(2):276-82 (2002).

Tapiero et al., "Prevention of pathologies associated with oxidative stress and dietary intake deficiencies: folate deficiency and requirements," Biomed. Pharmacother. 55(7):381-90 (2001).

Tchantchou et al., "Increased Transcription and Activity of Glutathione Synthase in Response to Deficiencies in Folate, Vitamin E, and Apolipoprotein E," J. of Neuroscience Research, 75:508-515 (2004).

Thal et al., "A 1-year controlled trial of acetyl-L-camitine in early-onset AD," Neurology 55:805-810 (2000).

Trolin et al., "Brain ATP:L-methionine S-adenosyltransferase (MAT), S-adenosylmethionine (SAM) and S-adenosylhomocysteine (SAH): regional distribution and age-related changes," European Neuropsychopharmacology, 4:469-477 (1994).

Yang et al., "Mechanisms of inactivation of human S-adenosylhomocysteine hydrolase by 5',5',6',6'-tetradehydro-6'-deoxy-6'-halohomoadenosines," Biochemistry. 39(49):15234-41 (2000).

Ekinci, Fatma J. et al., "Beta-Amyloid-induced calcium influx induces apoptosis in culture by oxidative stress rather tha tau phosphorylation," Molecular Brain Research, vol. 76:389-395 (2000).

Ekinci, Fatma J. et al., "Beta-Amyloid-Induced Tau Phosphorylation does not Correlate with Degeneration in Cultured Neurons," Journal of Alzheimer's Disease, vol. 2:7-15 (2000).

Ho, Pei I. et al., "Homocysteine potentiatesbeta-amyloid neurotoxicity: role of oxidative stress," Journal of Neurochemistry, vol. 78:1-6 (2001).

Ho, Pei I. et al., "Multiple Aspects of Homocysteine Neurotoxicity: Glutamate Excitotoxicity, Kinase Hyperactivation and DNA Damage," Journal of Neuroscience Research, vol. 70:694-702 (2002).

Mattson, Mark P. et al., "Folate and homocysteine metabolism in neural plasticity and neurodegenerative disorders," Trends in Neurosciences, vol. 26(3):137-146 (2003).

Mihalick, Shelia M. et al., "Folate and Vitamin E Deficiency Imipair Cogniti ve Performance in Mice Subjected to Oxidative Stress," NeuMolecular Medicine, vol. 4:197-201 (2003).

Ortiz, Daniela et al., "Apple juice prevents oxidative stress induced by amyloid-beta in culture," Journal of Alzheimer's Disease, vol. 6:27-30 (2004).

Rogers, E.J. et al., "Apple Juice Prevents Oxidative Stress and Impaired Cognitive Performance Caused by Genetic and Dietary Deficiencies in Mice," The Journal of Nutrition, Health & Aging, vol. 7(6):1-6 (2003).

Shea, Thomas B. et al., "17 beta-Estradiol alleviates synergistic oxidative stress resulting from folate deprivation and amyloid-beta treatment," Journal of Alzheimer's Disease, vol. 5:323-327 (2003).

Shea, Thomas B. et al., "Differential susceptibity of transgenic mice lacking one or both apolipoprotein alleles to folate and vitamin E deprivation," Journal of Alzheimer's Disease, vol. 4:1-5 (2002).

Shea, Thomas B. et al., "Efficacy of Vitamin E, Phosphatidyl Choline, and Pyruvate on Buffering Neuronal Degeneration and Oxidative Stress in Cultured Cortical Neurons and in Central Nervous Tissue of Apolipoprotein E deficient Mice," Free Radical Biology & Medicine, vol. 33(2):276-282 (2002).

Shea, Thomas B. et al., "Homocysteine and Dementia," N. Engl. J. Med., vol. 346(25):2007 (2002).

Shea, Thomas B. et al., "Homocysteine, folate deprivation and Alzheimer neuropathology," Journal of Alzheimer's Disease, vol. 4:261-267 (2002).

Shea, Thomas B. et al., "The S-Adenosyl Homocysteine Hydrolase Inhibitor 3-Deaza-Adenosine Prevents Oxidative Damage and Cognitive Impairment Following Folate and Vitamin E Deprivation in a Murine Model of Age-Related, Oxidative Stress-Induced Neurodegeneration," NeuroMolecular Medicine, vol. 5:173-182 (2004).

Tchantchou, F. et al., "Dietary Supplementation with Apple Juice Concentrate Alleviates the Compensatory Increase in Glutathione Synthase Transcription and Activity that Accompanies Dietary- and Genetically-Induced Oxidative Stress," The Journal of Nutrition, Health & Aging, vol. 8(6):492-496 (2004).

Tchantchou, Flaubert et al., "Increased Transcription and Activity of Glutathione Synthase in Response to Deficiencies in Folate, Vitamin E, and Apoliporpotein E," Journal of Neuroscience Research, vol. 75:508-515 (2004).

Tjiattas, Lindsay et al., "Folate deficiency and homocysteine induce toxicity in cultured dorsal root ganglion neurons via cytosolic calcium accumulation," Aging Cell, vol. 3:71-76 (2004).

Chan, A. et al., "Dietary and Genetic Compromise in Folate Availability Reduces Acetylcholine, Cognitive Performance and Increases Aggression: Critical Role of S-Adenosyl Methionine," The Journal of Nutrition, Health & Aging, vol. 12(4):252-261 (2008).

Chan, Amy et al., "Efficacy of a Vitamin/Nutriceutical Formulation for Early-stage Alzheimer's Disease: A 1-year, Open-label Pilot Study With an 16-Month Caregiver Extension," American Journal of Alzheimer's Disease & Other Dementias, vol. 23(6):571-585 (2009).

Dhitavat, Sirakarnt et al., "Acetyl-L-Carnitine Protects against Amyloid-Beta Neurotoxicity: Roles of Oxidative Buffering and ATP Levels," Neurochemical Research, vol. 27(6):501-505 (2002).

Dhitavat, Sirakarnt et al., "Differential efficacy of lipophilic and cytosolic antioxidants on generation of reactive oxygen species by amyloid-b," Journal of Alzheimer's Disease, vol. 3:525-529 (2001).

Dhitavat, Sirakarnt et al., "Folate, vitamin E, and acetyl-L-carnitine provide synergistic protection against oxidative stress resulting from exposure of human neuroblastoma cells to amyloid-beta," Brain Research, vol. 1061:114-117 (2005).

Remington, Ruth et al., "Efficacy of a Vitamin/Nutriceutical Formulation for Moderate-stage to Later-stage Alzheimer's disease: A Placebo-controlled Pilot Study," American Journal of Alzheimer's Disease & Other Dementias, vol. 24(1):27-33 (2009).

Shea, Thomas B., "Effects of Dietary Supplementation with N-Acetyl Cysteine, Acetyl-L-Carnitine and S-Adenosyl Methionine on Cognitive Performance and Aggression in Normal Mice and Mice Expressing Human ApoE4," Neuromol. Med., vol. 9:264-269 (2007).

Shea, Thomas B. et al., "Efficacy of Vitamin E, phosphatidyl choline and pyruvate on Abeta neurotoxicity in culture," J. Nutr. Health Aging, vol. 7(4):252-255 (2003).

Shea, Thomas B. et al., "Nanosphere-mediated delivery of vitamin E increases its efficacy against oxidative stress resulting from exposure to amyloid beta," Journal of Alzheimer's Disease, vol. 7(4):297-301 (2005).

Shea, Thomas B. et al., "Vitamin E deficiency does not induce compensatory antioxidant increases in central nervous system tissue of apolipoprotein E-deficient mice," Journal of Alzheimer's Disease, vol. 5:9-14 (2003).

Tchantchou, Flaubert et al., "Dietary Supplementation With 3-Deaza Adenosine, N-Acetyl Cysteine, and S-Adenosyl Methionine Provide Neuroprotection Against Multiple Consequences of Vitamin Deficiency and Oxidative Challenge," NeuroMolecular Medicine, vol. 6:93-103 (2004).

Tchantchou, Flaubert et al., "S-Adenosyl Methionine: A Connection Between Nutritional and Genetic Risk Factors for Neurodegeneration in Alzheimer's Disease," The Journal of Nutrition, Health & Aging, vol. 10(6):541-544 (2006).

Tchantchou, Flaubert et al., "S-Adenosylmethionine Mediates Glutathione Efficacy by Increasing Glutathione 5-Transferase Activity: Implications for S-Adenosyl Methionine as a Neuroprotective Dietary Supplement," Journal of Alzheimer's Disease, vol. 14:323-328 (2008).

* cited by examiner

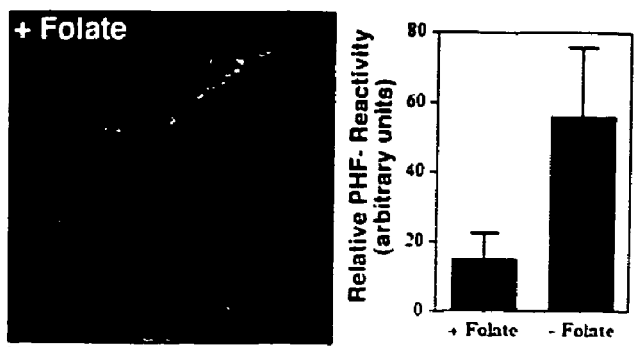
Fig. 1A
Fig. 1C
Fig. 1B
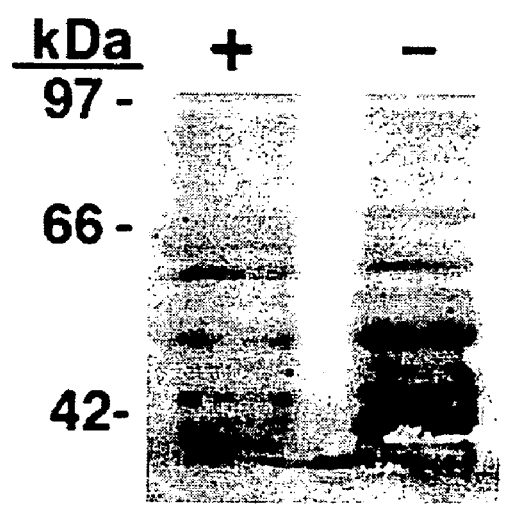
Fig. 2

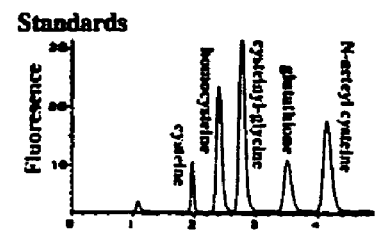
Fig. 18A
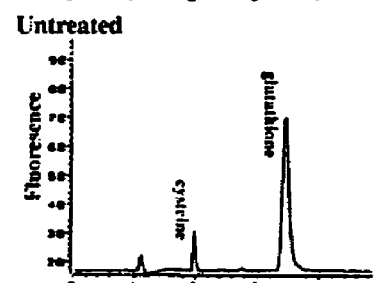
Fig. 18B
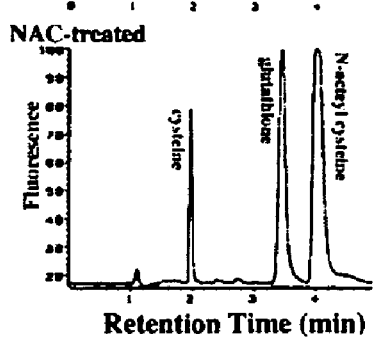
Fig. 18C
Fig. 18
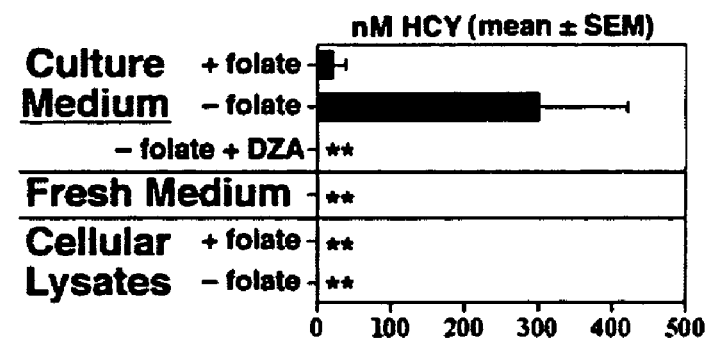
Fig. 19

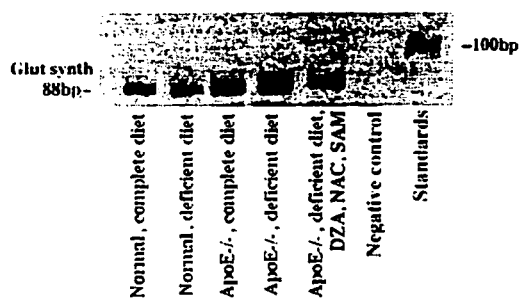
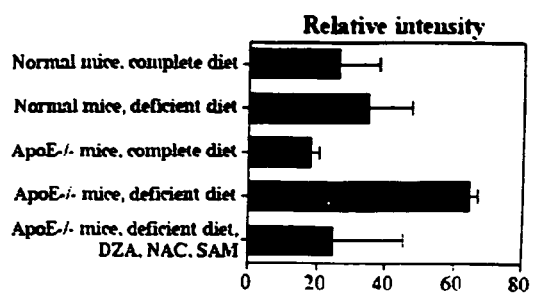
Fig. 23A          Fig. 23B
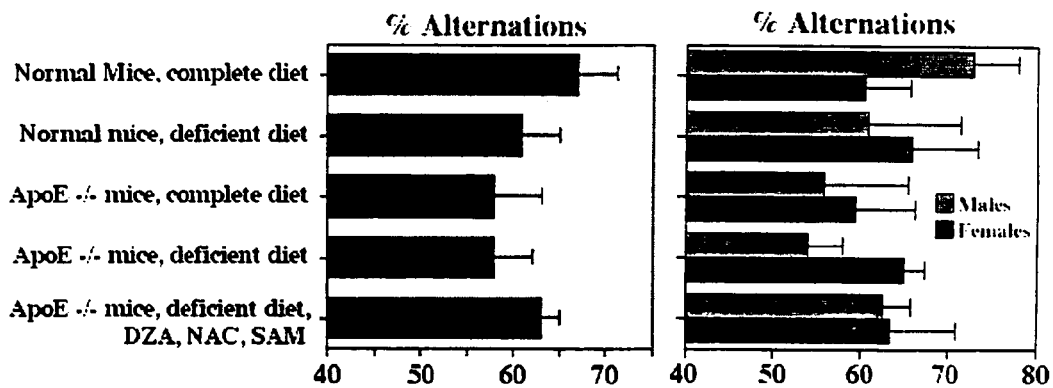
Fig. 24

FORMULATIONS FOR REDUCING NEURONAL DEGENERATION

CROSS-REFERENCE TO RELATED APPLICATION

This application claims priority from U.S. Provisional Patent Application No. 60/490,339 filed on Jul. 25, 2003. The contents of which are incorporated herein by reference in their entirety.

TECHNICAL FIELD

This invention relates to treatment of neurodegenerative disorders, and more particularly to Alzheimer's disease and Parkinson's disease.

BACKGROUND

Oxidative stress plays a role in neurodegeneration, regardless of etiology. Physical trauma or secondary effects of insult to the nervous system that result in ischemia can also result in serious damage from oxidative stress. The reduction of oxidative stress is therefore a target for therapeutic interventions for these disorders.

The etiology of Alzheimer's disease is not yet understood. Contributing factors and hallmarks of the disease include an aberrant accumulation of the beta-amyloid fragment (Abeta) of the large transmembrane amyloid precursor protein (APP), abnormal accumulation of calcium within neurons, generation of reactive oxygen species, and abnormal accumulation of phosphorylated forms of the microtubule associated protein, tau. Exposure to Abeta can induce rapid degeneration of cultured neurons. Abeta induces rapid calcium influx, which results in production or reactive oxygen species (ROS), which in turn causes greater accumulation of calcium in the cell. There is also an accumulation of phosphorylated tau. In vitro, phospho-tau is found in paired helical filaments (PHF), structures that persist even after neuronal degeneration and form the "tangles" characteristic of certain neurodegenerative diseases. The physiologic changes caused by Abeta generally result in neuronal death by apoptosis.

Most clinical trials and research related to potential treatments for Alzheimer's disease have examined the efficacy of single compounds, and some treatments have toxic side effects that can limit long-term use. Alzheimer's disease and some other neurodegenerative diseases develop over long periods of time (years). Accordingly, it is desirable that preventative measures and treatments be such that they can be administered over long periods of time without causing significant adverse side effects.

SUMMARY

The present invention relates, in part, to formulations and methods for treating and preventing neurodegenerative disorders, e.g., Alzheimer's disease and Parkinson's disease. Such formulations are also useful as supplements for culturing cells such as neurons. The invention includes two general formulations. One formulation (nutriceutical formulation) includes two or more of vitamin E, folate, and acetyl-L-carnitine (ALCAR). The second formulation (pharmaceutical formulation) includes two or more of N-acetyl cysteine (NAC; NALC), S-adenosyl methionine (SAM), and 3-deazaadenosine (DZA). These formulations inhibit the progressive loss of neurons in neurodegenerative disorders such as Alzheimer's disease and Parkinson's disease, as well as normal aging. The formulations can also be used or administered together, or one or more agents or components of one of the formulations can be combined with one or more of the agents of the other formulation.

Also described herein is an animal model that is useful for, e.g., identifying compounds that ameliorate biochemical or cognitive symptoms of neurodegenerative disorders such as Alzheimer's disease.

Accordingly, the invention relates to methods for treating a neurodegenerative disorder in a subject, such as a mammal. The method includes administering to the mammal (e.g., a human) an amount of a nutriceutical formulation effective to ameliorate the effects of neurodegeneration, such that the nutriceutical formulation contains at least two of the agents, folate, vitamin E, and ALCAR. The formulation can include an analog of an agent as a substitute for that agent. The formulation can be, for example, folate, vitamin E, and ALCAR. The mammal may be suffering from a neurodegenerative disorder such as, for example, Alzheimer's disease, Parkinson's disease, or amyotrophic lateral sclerosis (ALS). In some embodiments of the method, a level of reactive oxygen species (ROS) in the mammal is reduced compared to a reference level (e.g., of a mammal, e.g., a human, having no neurodegenerative disorder).

The invention also relates to compositions useful for treating neurodegenerative disorders that include at least two of the agents, folate, vitamin E, and ALCAR. The compositions can include an analog of an agent with or substituting for, that agent. The compositions can be, for example, a combination of folate, vitamin E, and ALCAR.

Also described herein are methods for culturing cells. The methods involve contacting the cells (e.g., neuronal cells such as cortical neurons or SH-SY-5Y cells) with a medium that contains at least two of the agents, folate, vitamin E, and ALCAR, or analogs of these agents. In some cases, the medium contains folate, vitamin E, and ALCAR. In some embodiments, the cells are grown in medium that does not contain folate.

In another embodiment, the invention relates to methods for treating neurodegenerative disorders (e.g., Alzheimer's disease, Parkinson's disease, or amyotrophic lateral sclerosis (ALS)) in a subject, such as a mammal (for example a human), in which an amount of a pharmaceutical formulation effective to ameliorate the effects of neurodegeneration is administered to the mammal. The pharmaceutical formulation includes at least two of the agents, 3-deaza-adenosine (DZA), N-acetyl-L-cysteine (NAC), and S-adenosylmethionine (SAM). In some cases, the pharmaceutical formulation includes all three agents DZA, NAC, and SAM. In some embodiments of the method, a level of ROS is reduced in the mammal compared to a reference level (e.g., an the level in an untreated and/or healthy mammal).

Also included are compositions useful for treating neurodegenerative disorders. The compositions include at least two of the agents, 3-deaza-adenosine (DZA), N-acetyl-L-cysteine (NAC), and S-adenosylmethionine (SAM). An analog of an agent can be used as a substitute for the agent. In some cases, the composition includes DZA, NAC, and SAM.

In another aspect, the invention also relates to methods for culturing cells (e.g., neuronal cells such as cortical neurons or SH-SY-5Y cells) in which the cells are contacted with a medium that includes at least two of the agents, 3-deaza-adenosine (DZA), N-acetyl-L-cysteine (NAC), and S-adenosylmethionine (SAM). An analog of an agent can be used as a substitute for the agent. In some cases, the medium contains DZA, NAC, and SAM. The cells used in the method can be grown in medium without folate.

In another aspect, the invention includes methods of treating a subject having a neurodegenerative disorder in which a therapeutic amount of a formulation that decreases homocysteine expression or activity is administered to the subject.

A nutriceutical formulation is a composition that includes at least two of the following agents: folate, vitamin E, and ALCAR. Such formulations reduce the amount of ROS in a cell. In general, a nutriceutical formulation includes ALCAR and either folate or vitamin E. In certain embodiments, the nutriceutical formulation contains all three agents.

A pharmaceutical formulation is a composition that includes at least two of the following agents: DZA, NAC, and SAM. Such formulations reduce the amount of ROS in a cell.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DESCRIPTION OF DRAWINGS

FIGS. 1A and 1B are a set of photographs of differentiated SH-SY-5Y cells cultured with or without folate and then stained to detect paired helical filament-1 (PHF-1).

FIG. 1C is a bar graph showing the results of densitometric analyses of PHF-1 immunoreactivity in the cells cultured with or without folate.

FIG. 2 is an image of an immunoblot showing staining of PHF-1 in extracts prepared from differentiated SH-SY-5Y cells cultured with or without folate.

FIGS. 18A to 18C are a set of HPLC traces detecting cysteine, glutathione, and N-acetyl cysteine extracted from SH-SY-5Y cells. FIG. 18A is a trace of 50 µM standards, FIG. 18B is a trace of cell extract from cells that were not treated with NAC, and FIG. 18C is a trace of cell extract from cells that were treated with NAC.

FIG. 19 is a bar graph showing the results of experiments in which homocysteine concentration was measured in SH-SY-5Y cells cultured in the presence or absence of folate and in the presence or absence of 25 µM DZA. Homocysteine concentrations are in nM. ** indicates undetectable concentrations of homocysteine within the limits of HPLC analyses; therefore ≦1 nM.

FIGS. 2-4). Additional mice received the deficient diet supplemented with DZA (0.4 g/kg total diet weight), SAM (80 mg/kg diet weight) and NAC (1 g/kg diet weight).

FIG. 23A is a representation of a gel showing PCR products of glutathione synthase from normal and ApoE−/− mice.

FIG. 23B is a bar graph that depicts the relative intensity of a scan of the 88 bp band of glutathione PCR product from normal and ApoE−/− mice that had undergone the indicated treatments.

FIG. 24 is a pair of bar graphs depicting the results of experiments in which normal and ApoE−/− mice that had been subjected to various dietary regimens were tested in a Y maze and the percentage of alterations were measured.

DETAILED DESCRIPTION

Figures 3A, 3B, 3C:
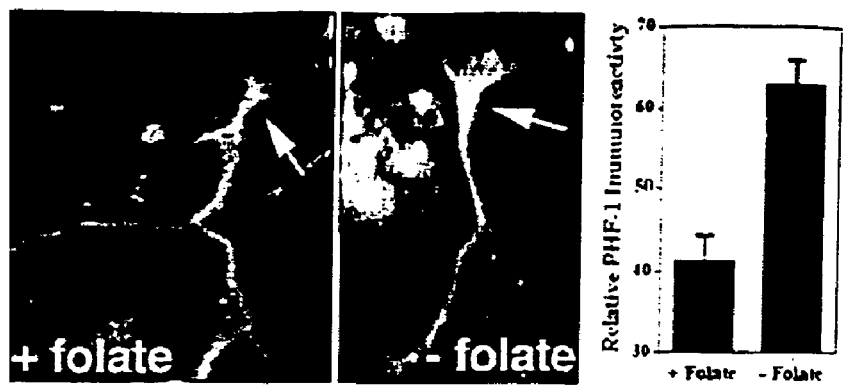
FIGS. 3A and 3B are a pair of photographs of murine cortical neurons cultured with or without folate and then stained with PHF-1.
FIG. 3C is a bar graph illustrating the results of densitometric analyses of PHF-1 immunoreactivity in the cells cultured with or without folate.

The invention involves the use of nutriceutical formulations and pharmaceutical formulations to treat and prevent disorders of the nervous system. Such disorders include neurodegenerative disorders, e.g., Alzheimer's disease, Parkinson's disease, and amyotrophic lateral sclerosis (ALS). These formulations are useful for minimizing the impact of oxidative stress on neurons, leading to neurodegeneration during normal aging. Thus, in one embodiment the formulations can be used as supplements to cell culture media for preventing or ameliorating the effects of oxidative stress. In other embodiments, the formulations are administered to animal or human subjects diagnosed with, or susceptible to, nervous system disorders.

Nutriceutical formulations include, at a minimum, at least two of the following agents, folate, vitamin E, and acetyl-L-carnitine (ALCAR). Pharmaceutical formulations include, at a minimum, at least two of the following agents, 3-dazaadenosine (DZA), N-acetylcysteine (NAC; NALC), and S-adenosyl methionine (SAM). The formulations described herein have been discovered to be useful for decreasing or reducing the level of reactive oxygen species (ROS) in cells, including cells exposed to Abeta, a peptide that is associated with induction of deleterious effects in Alzheimer's disease.

Importantly, combinations of the components of the formulations have been discovered to be more effective than the individual components for reducing ROS. This is, in part, because while the components can act individually to reduce ROS in cells, it was not previously appreciated that multiple pathways act to produce ROS in cells. Thus, treatment with combinations of agents that ameliorate the generation of ROS generated by multiple pathways provides a more effective treatment than previously used treatments. Such formulations have also been discovered to improve the cognitive abilities of mice carrying a mutation associated with a predisposition to Alzheimer's disease and subjected to environmental/dietary stress.

Nutriceutical formulations and pharmaceutical formulations can be used to treat and prevent neurological disorders in mammals (e.g., non-human primates and humans) especially neurodegenerative disorders, including Alzheimer disease, Huntington's disease, ALS, and Parkinson's disease. Nutriceutical formulations and pharmaceutical formulations are also useful for treating injuries to the nervous system such as those caused by physical trauma or ischemia and can be used to delay or prevent neurodegeneration that accompanies normal aging.

In Alzheimer's disease there is an increase in the production of ROS, an increase in cytosolic calcium influx, and an increase in the phosphorylation of tau protein. The new combinations of agents described herein attenuate the production of ROS, decrease cytosolic calcium influx, decrease the phosphorylation of tau protein, and prevent or inhibit neuronal death.

Without committing to any particular theory, it appears that these agents combine to ameliorate the effects of homocysteine, a neurotoxic, non-peptide molecule that can elicit production of ROS, and can increase cytosolic calcium influx, phosphorylation of tau protein, glutamate excitoxicity, DNA breakage, and neuronal death.

It is also demonstrated herein that various combinations of the agents prevent neurodegeneration in cultured neuronal cells both following treatment with Abeta and following folate deficiency. Furthermore, the combinations of these agents induce a decrease in ROS that significantly exceeds the effect of any single agent.

Nutriceutical Formulations

A nutriceutical formulation includes at least two of three agents: folate, vitamin E, and acetyl-L-carnitine (ALCAR); and the formulation must reduce ROS in neural cells. Such formulations can be used to ameliorate the effects of neurodegenerative disorders and trauma on neural cells, e.g., in a mammal such as a human. Examples of specific formulations include folate and ALCAR, ALCAR and vitamin E, folate and vitamin E, and a combination of all three agents.

ALCAR is an ester of the trimethylated amino acid L-carnitine, which is normally synthesized in human brain, liver, and kidney. ALCAR facilitates the uptake of acetyl-CoA to mitochondria during fatty acid oxidation and therefore enhances cellular energy production. ALCAR has neuroprotective effects in animal trials (Brooks et al., 1998, Int. Psychogeriatr., 10:193-203; Thal et al., 1996, Neurology, 47:705-711) and studies have suggested that ALCAR is effective against Abeta neurotoxicity (Scorziello et al., 1997, Neurochem. Res., 22:257-265). Folate has been shown to buffer oxidative damage in the central nervous system (Tapiero et al., 2001, Biomed. Pharm., 55:381-390), and its absence is associated with neurodegeneration (Serot et al., 2001, J. Neural. Transm., 108:93-99; Snowdon et al., 2000, Am. J. Clin. Nutr., 71:993-998).

Nutriceutical formulations can be prepared using methods known in the art, and contain ranges of the two or three agents. For example, the amount of folate to be administered for therapeutic use is from between about 200 to 2000, e.g., 400 to 1500, or 500 to 1000 μg/day. Specific dosages within this range include 200, 350, 500, and 100 μg/day.

The concentration of vitamin E to be administered is from between about 50 to 3,000 I.U./day, e.g., 100 to 2,000, 250 to 1500, 500 to 1000, 100 to 400, 250, 750, 500, 1000, or 1500 I.U./day. The amounts administered depend, in part, on the form of vitamin E administered, for example the bioavailability of the form. The vitamin E used in a nutriceutical formulation can be any bioactive form of vitamin E including alpha-tocopherol, gamma-tocopherol, and vitamin E esters such as vitamin E succinate and vitamin E acetate, vitamin E salts such as vitamin E phosphate, and other water soluble forms of vitamin E (e.g., TROLOX®).

The concentration of ALCAR is from between about 200 to 4000 mg/day, e.g., 500 to 3000, 1000 to 2000, 250, 750, or 1000 mg/day. Although convenient for administration, it is not necessary for the agents or components of the nutriceutical formulations to be compounded together for administration to a mammal. Instead, they can be administered concurrently, or in close enough succession so that the desired dosage level for all components is achieved in the bloodstream at the same time.

Pharmaceutical Formulations

A pharmaceutical formulation includes at least two of three agents: DZA, NAC, and SAM; and the formulation must reduce ROS in neural cells (as described herein, e.g., in the examples herein). Such formulations can be used to ameliorate the effects of neurodegenerative disorders and trauma on neural cells, e.g., in a mammal such as a human. Specific examples of pharmaceutical formulations include DZA and NAC, DZA and SAM, NAC and SAM, and a combination of all three agents.

Pharmaceutical formulations can be prepared using methods known in the art. For example, the amount of DZA administered for therapeutic use is from between about 20 to 500 mg/day, e.g., 50 to 250, 75 to 150, or 100 mg/day. The concentration of SAM is from between about 400 to 2000 mg/day, e.g., about 500, 750, 1000, 1250, or 1500 mg/day. The NAC is administered at about 200 mg to 2000 mg/day, e.g., about 500, 750, 1000, or 1500 mg/day. Although convenient for administration, it is not necessary for the components of pharmaceutical formulations to be compounded together for administration to a mammal.

DZA and other structural based adenosine analogues and other compounds that inhibit S-Adenosylhomocysteine hydrolase (EC 3.3.1.1) can be included in pharmaceutical formulations and, e.g., diminish the production of intraneuronal homocysteine synthesis. Inhibition may be competitive or non-competitive, reversible or irreversible, and in either a general or specific manner. Compounds include type I mechanism based inhibitors, which are typically adenosine derivatives that are irreversibly oxidized to their 3'-keto product with the associated conversion of the active NAD+ form of SAH hydrolase to the inactive NADH form or type II inhibitors that are chemically converted by SAH hydrolase to reactive intermediates that covalently alter the enzyme (Yang X et al., 2000, Biochemistry, 39:15234-15241).

Also useful in formulations are N-acetyl-L-cysteine and other chemically similar compounds that increase intracellular cysteine levels, thus providing the amino acid for glutathione synthesis.

The above concentrations can be further determined using standard procedures in, e.g., phase III clinical trials.

The new pharmaceutical formulations are also useful for treatment of dietary or genetic deficiencies in folate metabolism.

Also included in the invention are combinations of two or more agents used in nutriceutical formulations and pharmaceutical formulations, e.g., combinations of at least two of the following agents; DZA, NAC, SAM, vitamin E, ALCAR, and folate. As with the individual components in the neutriceuticals and pharmaceuticals, the components used in the combined form can be compounded into one dosage form, e.g., a tablet or pill, or can be administered concurrently or successively to achieve the desired dosage level in the bloodstream at the same time.

Measurement of Reactive Oxygen Species (ROS)

Reactive oxygen species (ROS) are chemical species harboring free radicals. ROS are measured in test systems to evaluate the ability of a nutriceutical formulation or a pharmaceutical formulation to reduce free radical production. For example, a method that uses electrochemical detection of dihydroxybenzoic acids (DHBA) and salicylate, available from ESA, Inc. (Chelmsford, Mass.) can be used to test free radical production in neuronal cultures in the presence or absence of a nutriceutical formulation or a pharmaceutical formulation. Formulations that lower free radical concentrations in cells are useful for treating neural disorders such as Alzheimer disease or ischemia, in which overproduction of free radicals is undesirable.

Damage resulting from the generation of intracellular reactive oxygen species can also be quantified using a TBAR assay (Ohkawa et al., Anal. Biochem., 95:351-358, 1979). This method is used to determine cellular lipid hydroperoxides in cultured cells by thiobarbituric acid reaction. Lipid hydroperoxides break down to malondialdehyde and other aldehydes. These react with thiobarbituric acid in a mildly acidic environment, which results in formation of a chromophore. The resulting chromophore is measured by light absorption or fluorescence techniques.

Glutathione Synthase

As described infra, glutathione is increased in folate deficiency and iron challenge. There is also a concomitant increase in glutathione synthase transcription. To assay this aspect of deficiencies found to be associated with neurodegeneration, as well as to assay the effect of a test compound for its ability to decrease glutathione, glutathione synthase mRNA, glutathionase synthase activity, or glutathione itself can be measured. Glutathione can be assayed using methods known in the art and as described herein, e.g., using HPLC. Methods of assaying glutathione mRNA are known as are methods of measuring glutathione synthase activity. For example, the enzymatic activity can be determined using a spectrophotometric measurement of the oxidation rate of NADPH at 340 nm. The reaction buffer contains 100 mM Tris-HCl (pH 8.2), 50 mM KCl, 20 mM $MgCl_2$, 5 mM Na phosphoenolpyruvate, 0.2 mM NADH, pyruvate kinase, lactic acid dehydrogenase, and glutathione synthetase substrate (to a final volume of 1 mL). The assay is initiated by addition of the sample extract.

Methods of Testing Nutriceutical Formulations and Pharmaceutical Formulations

In general, a nutriceutical formulation or a pharmaceutical formulation is formulated by combining appropriate concentrations of stock agent (e.g., in solution or solid) of the components in a medium. The components can be administered together, in rapid succession, or at intervals. A composition is tested to determine whether it is an effective nutriceutical formulation or pharmaceutical formulation in an in vitro cell culture system of primary, secondary, or immortalized neural cells cultured under conditions that exhibit at least some of the biochemical characteristics of a neurologic disorder. Examples of such cells and methods of evaluating the effects of the formulations are described below. Biochemical and physical criteria can be used to measure the ability of a nutriceutical formulation or a pharmaceutical formulation to ameliorate adverse effects associated with a disorder in these cell culture systems. For example, a decrease in reactive oxygen species is indicative of effectiveness. In some cases, cells are treated with Abeta and the ability of a formulation to ameliorate at least one deleterious cellular response to Abeta is measured. Deleterious responses to Abeta include increased ROS, calcium influx, increased phosphorylation of tau, and apoptosis. A formulation that decreases ROS and/or a deleterious cellular response to Abeta is a candidate nutriceutical formulation or pharmaceutical formulation, because it has been demonstrated that quenching of ROS renders Abeta exposure benign (Ekinci et al., 1999, J. Biol. Chem., 274: 30322-30327).

Other methods can be used to evaluate formulations. For example, other useful methods measure expression of stress-induced genes using methods known in the art.

Use of Animal Models for Testing Nutriceutical Formulations and Pharmaceutical Formulations Animal models of neurologic disease are useful for evaluating the efficacy of a nutriceutical formulation or pharmaceutical formulation. After a nutriceutical formulation or a pharmaceutical formulation is shown to confer a decrease in ROS/or a reduction in an adverse cellular response to Abeta treatment in vitro, a formulation can also be evaluated in vivo using an animal model of a specific neurologic disorder. Examples of such model systems are a transgenic mouse model for familial ALS that has a defective Cu, Zn superoxide dismutase gene, and a rat model of ALS in which axotomy of facial axons in neonatal rats causes retrograde cell degeneration (Cleveland et al., Neurology, 47 (Suppl 2): S54-61, 1996; Dal Canto, Clin. Neurosci., 2:332-337, 1996; and Price et al., Ciba Found. Symp., 196:3-13, 1996). Animal models for Alzheimer's disease can also be used to evaluate the ability of the new a formulations to treat this disease. Examples of such models are the PDAPP (V717F) transgenic mouse (Johnson-Wood et al., Proc. Natl. Acad. Sci. USA, 94:1550-1555, 1997), and other transgenic mouse lines in which expression of the amyloid precursor protein (APP) gene is affected (Reaume et al., J. Biol. Chem., 271:23380-23388, 1996; Hsiao et al., Science, 276:99-102, 1996; and Games et al., Nature, 373:523-527, 1995).

In addition, animal models of Parkinson's disease are known in the art and can be generated, for example, by treating young animals with 1-methyl-4-phenyl-1,2,3,6-tetrahydropyridine (MPTP; e.g., Tatton, Mov. Disord., 8 Suppl 1:, S20-30, 1993; and Przedborski et al., Proc. Nat. Acad. Sci., USA, 93:4565-4571). Animal models are also used for studying the ability of formulations to affect spinal cord transplants. Such models are known in the art (e.g., Tessler et al., Adv. Neurol., 72:291-303, 1997).

As an example for how an animal model can be used, a transgenic mouse that expresses a neurofilament-beta galactosidase fusion protein (Eyer and Peterson, 1994, Neuron 12:389-405) can be used to evaluate the effects of a formulation on neurofilament phosphorylation and localization. Such mice do not carry out complete axonal transport of neurofilaments, but instead accumulate neurofilaments within neuronal perikarya. A nutriceutical formulation or pharmaceutical formulation is administered to such a mouse and the gross motor function and cellular morphology, especially the distribution of neurofilaments within cells, is evaluated over time in treated and untreated mice. Decreased accumulation of neurofilaments within the perikarya of neurons indicates that the nutriceutical formulation or pharmaceutical formulation is useful for correcting this defect.

Nutriceutical formulations or pharmaceutical formulations can also be evaluated for their efficacy in preventing or ameliorating the effects of Alzheimer disease using an animal model, examples of which are provided herein. In one example, a transgenic mouse that overexpresses the 695-amino acid form of human Abeta appears to have normal learning and memory at 3 months of age (Hsiao et al., Science, 274:99-102, 1996). However, by 9 to 10 months, these animals are impaired. This pattern mimics the symptoms of Alzheimer disease in humans. The effects of a nutriceutical formulation or pharmaceutical formulation on ameliorating behavioral and biochemical symptoms in these mice are evaluated after administering a nutriceutical formulation or pharmaceutical formulation to these mice both early in life and after symptoms begin to develop. Mice are evaluated for the development or progression of learning and memory disorders as well as for pathophysiologic and biochemical abnormalities such as the presence of plaques in cortical and limbic structures of the brain. Prevention of the onset or progression of symptoms, or the amelioration of existing symptoms indicates that the nutriceutical formulation or pharmaceutical formulation is effective for treating Alzheimer disease or Parkinson's disease in humans.

Other animal models in which the animal carries one or more mutations associated with a neurologic disorder such as mice that are ApoE-/-, a genotype associated with Alzheimer's disease, are useful. Animals with or without such mutations can be subjected to dietary/environmental distress such as folate deprivation or inclusion of dietary iron to induce biochemical and/or cognitive symptoms that can be measured, e.g., in assays determining the efficacy of nutriceutical or pharmaceutical formulations.

Other parameters of neuronal stress that are known in the art, examples of which are described herein, can be studied using known tests such as those described herein to evaluate the ability of a nutriceutical formulation or pharmaceutical formulation to ameliorate symptoms associated with a neurodegenerative disorders. Such tests include measuring the presence of ROS, or TBARs resulting from same, in neuronal tissue in various transgenic mice models of Alzheimer's disease or Parkinson's disease, as well as comparisons of younger and aged normal mice.

In general, to evaluate whether a nutriceutical formulation or pharmaceutical formulation is useful for treating a neurologic disorder, an animal or human with symptoms or predisposition to a neurological disorder is treated with the formulation. After an appropriate treatment regime, the animal or human is examined for improvement or arrest of symptoms of the disorder. In the case of ALS, this can be stopping or slowing motor neuron degeneration. In Alzheimer disease, positive effects of a formulation can include an improvement of memory, inhibition or arrest of progressive memory loss, decrease in the concentration of Abeta in spinal fluid, reduction in the rate of accumulation of amyloid plaques and/or neurofibrillary tangles, and reduction of ROS. Improvements detected in Parkinsonian conditions can be slowing or stopping degradation of motor function, particularly improvement of bradykinesia and akinesia, and decreased loss of cells in the substantia nigra. In all cases, animal models and cell culture systems are also useful for evaluating possible deleterious effects of a formulation.

The effects of a nutriceutical formulation or pharmaceutical formulation on neural cells, neurons, higher function, and behavior can also be evaluated in a human. In general this occurs after testing in an animal model. In such tests, for example, administration of an effective amount of a formulation to a human subject diagnosed with Alzheimer disease will result in slowing or stopping the progression of symptoms such as memory loss, poor or decreased judgment, or personality, mood, and behavioral changes. The levels of ROS in the blood or cerebral-spinal fluid (CSF) can also be measured. Effective formulations decrease ROS. In patients with ALS, the progression of symptoms such as muscular weakness and atrophy are slowed or halted. Successful treatment of patients with Parkinson's disease is indicated by the slowing or stopping of the progression of symptoms such as muscular rigidity, resting tremor, postural instability. In all disorders, physical, behavioral, and biochemical evaluation is performed using methods known in the art (e.g. *The Merck Manual, Sixteenth Edition,* 1992, R. Berkow, ed., Merck Research Laboratories, Rahway, N.J.).

Considerations for Administration of Formulations for Neurologic Disorders

One difficulty encountered with potential treatments for neurodegenerative disorders is that the compounds may not cross the blood-brain barrier or do so only in the presence of additional agents. The agents used in pharmaceutical formulations, DZA, NAC, and SAM, have been shown (directly or indirectly) to cross, or are predicted to cross, the blood-brain barrier (BBB). NAC has been reported to enter or have effects in the CNS, as has SAM. DZA is a nucleoside analog and nucleoside analogs have been shown to enter the nervous system ((Miserere et al., Pharm Rees (1994); 2:324-330; and Thomas et al., J. Pharmacol. Exp. Ther. (1997); 281:1211-1218) and many other analogs have been demonstrated to cross the BBB (Hoeterey et al. 1991, Drug Metab. Dispos., 19:907-912; Yang et al., 1997, Pharm. Res., 14:865-872). Moreover, the BBB becomes compromised and more permeable during oxidative stress (Argawal and Shulka, 1999, Neurochem. Res., 24:1507-1514), thus the agents used in nutriceutical and pharmaceutical formulations are likely to cross the blood-brain barrier in affected individuals. Furthermore, nutriceutical formulations and pharmaceutical formulations can be effective even if the agents do not cross the blood-brain barrier, because they can cause a reduction of a total body burden of reactive oxygen species, thus reducing the level of reactive oxygen species in the brain.

Formulations and Use

The new nutriceutical formulations and pharmaceutical formulations for use in accordance with the present invention can be formulated in a conventional manner using one or more physiologically acceptable carriers or excipients.

Agents used in the formulations and their physiologically acceptable salts and solvates can be prepared for administration by various methods. For example, administration can be parenteral, e.g., intravenous, subcutaneous, intramuscular, intracranial, intraorbital, ophthalmic, intraventricular, intracapsular, intraspinal, intracisternal, intraperitoneal, transmucosal; or administration can be oral. The compounds can be formulated in various ways, according to the route of administration.

For oral administration, the formulations can take the form of, for example, tablets or capsules, prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art.

Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin may serve this function, or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound.

For buccal or sublingual administration the formulations can take the form of tablets or lozenges formulated in conventional manner.

The formulations can be prepared for parenteral administration by injection, for example, by bolus injection or continuous infusion. Formulations for injection can be presented in unit dosage form, for example, in ampoules or in multi-dose containers, with an added preservative. The formulations can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, for example, sterile pyrogen-free water, before use.

The formulations can also be prepared in rectal compositions such as suppositories or retention enemas, for example, containing conventional suppository bases such as cocoa butter or other glycerides.

The formulations can also be provided as a depot preparation. Such long acting formulations may be administered by implantation (for example subcutaneously or intramuscularly) or by intramuscular injection. Thus, for example, the formulations can be prepared with suitable polymeric or hydrophobic materials (for example as an emulsion in an acceptable oil) or ion exchange resins, or as sparingly soluble derivatives, for example, as a sparingly soluble salt.

Because the action of a nutriceutical formulation or a pharmaceutical formulation can be in the central nervous system, delivery techniques can be designed to permit the formulation to cross the blood-brain barrier or to enhance the ability of the formulation to cross the blood-brain barrier. Such techniques are known in the art (for example, see PCT WO 89/10134, Cloughesy and Black, J. Neurooncol., 26:125-132, 1995; and Begley, J. Pharm. Pharmacol., 48:136-146, 1996, all of which are incorporated herein in their entirety). Components of a formulation can also be modified (e.g., chemically) using methods known in the art to facilitate their entry into the CNS.

In some cases, it may be desirable to deliver a nutriceutical formulation or a pharmaceutical formulation directly to the nervous system, especially when one or more components of a formulation do not cross the blood-brain barrier. Examples of such methods are intraventricular injection (Kordower et al., Exp. Neurol., 124:21-30, 1993) or installation of an osmotic pump (e.g., an Alzet® pump). Another example of such a method is to surgically place an Omaya reservoir-shunt with in-line filter into the cisternal space. A nutriceutical formulation or a pharmaceutical formulation in an appropriate excipient (e.g., phosphate-buffered saline) is instilled into the shunt by injection on a prescribed basis. In all cases, consideration is given to the appropriate formulation used for specific forms of delivery.

For administration by inhalation, a nutriceutical formulation or a pharmaceutical formulation is delivered, for example, as an aerosol spray with the use of a suitable propellant, for example, dichlorodifluoromethane, trichlorofluoromethane, dichlorotetrafluoroethane, carbon dioxide, or other suitable gas. Other suitable methods of nasal delivery known in the art can be used, including those that facilitate delivery of a predetermined dosage.

The formulations can be presented in a pack or dispenser device, which may contain one or more unit dosage forms containing the active ingredient. The pack may, for example, comprise metal or plastic foil, such as a blister pack. The pack or dispenser device can be accompanied by instructions for administration.

The therapeutic formulations of the invention can also contain a carrier or excipient, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol.

Methods useful for making formulations are known in the and can be found in, for example, *Remington's Pharmaceutical Sciences* (Gennaro, ed., Williams & Wilkins, Baltimore, Md.).

It is not necessary for all of the components of a nutriceutical formulation or a pharmaceutical formulation to be administered in the same excipient, in the same form, or delivered at precisely the same time during a day. However, the components should be administered so they are present in the treated subject at the same time (e.g., present in a cell that is the target of treatment), and thus, one formulation, including all three components, is generally provided in a convenient dosage form. This condition of treatment can be ascertained by assaying the appropriate body fluid (e.g., blood, plasma, serum, or cerebrospinal fluid) for the presence of components of a formulation or their metabolites. When monitoring the concentrations of agents, attention must be paid to differential accumulation of agents and/or their metabolites in the particular body fluid being tested. For example, folate has been reported to be concentrated fourfold within spinal fluid over that observed within plasma; moreover, the ability to concentrate folate within central nervous tissue declines in Alzheimer's disease (Snowdon et al., 2000, Am. J. Clin. Nutr., 71:993-998).

Other Uses

A nutriceutical formulation or pharmaceutical formulation can also be used to promote neuronal survival, and minimize secondary degeneration of endogenous neurons that is due to trauma.

The new nutriceutical formulations and pharmaceutical formulations can also be used to prevent or treat ischemia. For example, they can be administered as described herein in conjunction with procedures and devices such as transplantation (e.g., of neural tissue), implantation, and prosthetics. Administration can be systemic or directly to the site susceptible to ischemia such as by a shunt to a surgical site. Appropriate concentrations of the components of a nutriceutical formulation or a pharmaceutical formulation to be used for this purpose can be determined, for example, using methods described herein in model systems known in the art and in animal and human patients.

The specific examples employing a nutriceutical formulation or a pharmaceutical formulation that are described in detail below, which, while not limiting the scope of the invention described in the claims, provide additional guidance for the use of nutriceutical formulations and pharmaceutical formulations.

EXAMPLES

Example 1

Preparation of Nutriceutical Formulations and Pharmaceutical Formulations

Nutriceutical formulations and pharmaceutical formulations are prepared from stocks of the individual components. The following stock solutions were used for preparing nutriceutical formulations used in experiments described infra: folate at 200 mg or more in 100 mM potassium phosphate buffer pH 7.0; alpha-tocopherol (vitamin E) at 200 IU/ml in ethanol; and ALCAR at 200 mM dissolved in 100 mM potassium phosphate buffer pH 7.0.

For preparing pharmaceutical formulations, the following stock solutions were used:
  100 mM DZA dissolved in 100 mM potassium phosphate buffer pH 7.2.
  200 mM NAC dissolved in 50 mM disodium EDTA pH adjusted to 7.0 with NaOH.
  100 mM SAM dissolved in 100 mM potassium phosphate buffer pH 7.2 and 50 mM disodium EDTA.

In the cell culture experiments described below, aliquots of the stock solutions are combined in a standard commercial culture medium such as Dulbecco's modified Eagles Medium (DMEM) or DMEM without folate. The stock solution is then filtered through a 0.22 µM sterile filter before use.

For administration to an animal or human, the stock solutions are diluted in a standard solution, for example, in buffered saline, then sterilized by filtration or other suitable means.

Example 2

Cell Cultures and Treatment Regimes

Cultured cells were used to test individual agents and formulations. In general, SH-SY-5Y human neuroblastoma cells were cultured in DMEM (Cellgro) containing 10% fetal bovine serum in 5% $CO_2$. Cultures were differentiated for seven days with 10 µM retinoic acid, during which time the cells elaborated extensive neurites that exhibit characteristics of axons.

For treatments with Abeta, differentiated cultures were transferred to medium without serum and treated for two hours with 20 µM Abeta$_{25-35}$ (Sigma Chemical Co., St. Louis, Mo.). In experiments in which vitamin E was added, vitamin E was added to cultures at a concentration of 0.15 ng/ml as α-tocopherol (Sigma Chemical Co., St. Louis, Mo.). In experiments calling for treatment of cell cultures with N-acetyl cysteine (NAC; NALC), cultures were treated with 10 mM NAC (Sigma Chemical Co., St. Louis, Mo.) after the culture was grown for two hours in serum-free medium.

Intracellular reactive oxygen species (ROS) were monitored as described in Ekinci et al., 1999 (J. Biol. Chem., 274:30322-30327). Briefly, cells were incubated for 30 minutes with dichloro-fluorescein diacetate (DCFD; acetoxymethyl ester; Molecular Probes, Inc., Eugene, Oreg.), which is used to detect intracellular peroxide levels. Incubation was followed by rinsing of cultures in serum-free medium and immediate capture of images using UV optics. Images were captured under epifluorescent and phase-contrast illumination using a DAGE CCL-72 cooled CCD camera via a Scion LG-3 frame grabber operated by NIH Image (see the Internet at rsb.info.nih.gov/nih-image). Images were then stored as PICT files on a Macintosh Power PC 7100AV for subsequent analysis. At least 100 cells in randomly-selected fields from duplicate cultures derived from multiple experiments were scored for fluorescent intensity using NIH Image analysis software. Representative background areas devoid of cells were similarly analyzed and subtracted from cell values to yield net densitometric values. All fields for each individual assay were illuminated, captured, and processed under identical settings. Corresponding phase-contrast images were obtained. Cell aggregates were excluded from the assays; only individual cells were quantified. Values were exported to Excel for statistical analyses using Student's t test.

For immunocytochemistry to detect paired helical filament-1 (PHF-1) staining (as an index of tau phosphorylation), cells were fixed for 15 minutes with 4% paraformaldehyde in 0.1 M phosphate buffer and immunostained by sequential reaction with a mouse monoclonal PHF-1 antibody that was raised against tau from paired helical filaments isolated from the brains of Alzheimer disease patients. Incubation with PHF-1 antibody was followed by rhodamine conjugated goat anti-mouse IgG and visualization using methods known in the art.

Levels of externalized phosphatidylserine (PS) were used as a measure of apoptosis (Rimon et al., 1997, J. Neurosci. Res., 48:563-570). Briefly, cultures were subjected to treatments then rinsed with PBS and incubated with 10 μl/ml merocyanine (Upstate Biotech, Lake Placid, N.Y.), followed by examination under rhodamine optics (Ekinci et al, 1999, J. Biol. Chem., 274:30322-30327). Prior studies have confirmed that the percentage of cells demonstrating increased externalized PS corresponds to the number that undergo eventual overt degeneration.

Example 3

Folate Deficiency Induces Rapid Accumulation of Phospho-tau Within Neuronal Perikarya Critical dietary deficiencies have been shown to induce homocysteinemia. In particular, folate deficiency may induce pathological accumulation of homocysteine (Fiskerstrand et al., 1997, J. Pharmacol. Exp. Ther. 282:1303-1311). To investigate the potential influence of folate deficiency on homocysteine levels and indicia of neurologic disease (e.g., the formation of phospho-tau), differentiated SH-SY-5Y cells and murine cortical neurons were made folate-deficient. In these experiments, SH-SY-5Y cells were cultured in folate-deficient Dulbecco's Modified Essential Medium (DMEM; Sigma) in the absence of serum for two hours. Cortical neurons were prepared from 12 day embryonic C57/B16 day old mice using known methods.

The cortical neurons were cultured for 3 days in neurobasal medium with B27 supplements (Ekinici et al., 1999, J. Biol. Chem., 274:30322-30327). The medium was then changed to either serum-free DMEM+B27 supplements containing folate or serum-free DMEM+B27 supplements that lacked folate.

Both the SH-SY-5Y cultures and the cortical neurons were processed for PHF-1 (paired helical filament 1) immunofluorescence using known methods (Ekinci et al., 1999 supra). Control cells cultured in the continued presence of normal folate levels were also processed. Phospho-tau was also examined using immunoblot analysis. For these experiments, differentiated SH-SY-5Y cells were cultured in the presence or absence of folate and then harvested into 1% Triton X-100® in 50 mM Tris-HCl (pH 6.8), 5 mM EDTA, 50 μg/ml leupeptin, 1 mM phenylmethylsulfonyl fluoride (PMSF), and 1 mM NaF, and 1 mM Na vanadate. The homogenates were sedimented at 13,000×g for 15 minutes and the resulting supernatant was electrophoresed, blotted, and the blot stained for PHF-1 using known methods.

Examination of the PHF-1 stained cells, even after a short period of folate deficiency (two hours), showed that there was a marked increase in perikaryal phospho-tau as reflected by PHF-1 immunoreactivity. Densitometric analyses (using NIH Image Analysis Software; Ekinci et al., 1999, supra) revealed average increases of 3.5-fold and 1.5-fold in PHF-1 immunofluorescence in both SH-SY-5Y and cortical cells (FIGS. 1-3). There was a focal increase within the area at the base of the major neurite that was visibly increased more than the overall cellular average increase in both culture types (arrows; FIGS. 1 and 3). Although Abeta and altered kinase activities have previously been shown to increase PHF-1 immunoreactivity in these cell types, PHF-1 immunoreactivity under these conditions remained dispersed throughout the perikaryon (Ekinci and Shea, 1999, supra, Ekinci and Shea, 2000, J. Alz. Dis., 2:7-12).

The increase in PHF-1 immunoreactivity following folate deprivation was confirmed by immunoblot analyses of SH-SY-5Y cultures (FIG. 2). Additional cultures were immunostained with monoclonal antibody 5E2, which reacts with tau independently of its phosphorylation state. These analyses demonstrate that total tau levels were not altered by this relatively short-term (two hour) deprivation of folate. These data also indicate that the initial consequences of folate deprivation include specific alterations in tau phosphorylation/dephosphorylation cycles.

The accumulation of phospho-tau following folate deprivation was reversed within two hours following restoration of folate to SH-SY-5Y cells. Folate deprivation for 24 hours induced an average 29% increase in phospho-tau; however, when these cultures received medium containing folate, PHF-1 levels in these cells returned to control levels within four hours (Table 1).

These data demonstrate that folate can be used to decrease accumulation of phospho-tau.

TABLE 1

Folate deprivation induces a reversible increase in tau phosphorylation

| Culture Conditions | Mean ± SEM | P value vs. control | % increase in phospho-tau compared to control |
|---|---|---|---|
| +Folate 4 hr | 40.3 ± 3.9 | — | — |
| +Folate 24 hr | 38.1 ± 3.1 | 0.56 | −5.5% |
| −Folate 4 hr | 52.0 ± 3.4 | 0.01 | 29% |
| −Folate 24 hr | 39.7 ± 2.6 | 0.71 | −1.5% |

Example 4

Folate Deficiency Depletes Intracellular Glutathione and Increases Intracellular ROS Analyses were undertaken to identify additional effects of folate deficiency on neural cells. HPLC analysis was used to monitor the amount of reduced and oxidized glutathione in cells cultured in the presence and absence of folate. Glutathione levels were quantified in homogenates of SH-SY-5Y cells. Cultures were rinsed twice with Tris-buffered saline (TBS), scraped from the plate in a small volume of TBS and homogenized on ice. Medium was also utilized for analysis of HCY along with cellular lysates, since HCY is normally exported from cells. Homogenates (100 µl) were reduced by mixing with 50 µl of 100 µM N-acetylcysteine or with 30 µl of 30 µM cystamine (as an internal standard) and 10 µl of tricarboxyethylphosphine (100 mg/ml in 0.05 M HCl). Samples were vortexed, incubated at room temperature for 30 minutes, then centrifuged at 10,000×g for 10 minutes. 80 µl of the resulting supernatant were combined with 160 µl of 2 M boric acid/4 mM EDTA (pH 10.5), followed by 80 µl of 1.0 mg/ml SBDF [7-fluorobenzo-2-oxa-1,3-diazole-4-sulfonate] in boric acid/EDTA buffer). Samples were mixed, incubated for 60 minutes at 60° C., equilibrated to reach temperature, and 50 µl of the sample was then injected into a Hewlett Packard model 1090 HPLC, which is used with a 1046A fluorescence detector and a Hewlett Packard 4.6×60 mm high-speed analytical column packed with 3 µM ODs (C18) Hypersil silica. The mobile phase consisted of methanol/0.2 M acetate buffer pH 4.0 (2/98 by volume). Glutathione concentrations were then determined by comparison of peak area ratios of glutathione to the internal standard N-acetylcysteine in the sample compared to peak areas obtained for a glutathione standard curve. Samples were derived from 3-4 normal and 3-4 ApoE−/− mice for each dietary condition, from $\geq 2$ independent experiments (total $n \geq 6$ for each diet for both experiments).

Figure 4:
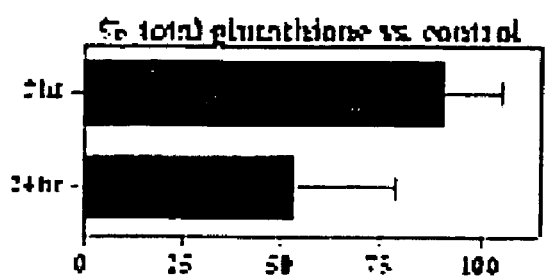
FIG. 4 is a bar graph that depicts the results of HPLC analysis for glutathione in cell extracts from SH-SY-5Y cells that were cultured for 2 or 24 hours in the presence or absence of folate. The data are expressed as a percentage of glutathione in folate-deprived cells compared to a control in which cells were grown in the presence of folate.

HPLC analyses revealed a marked shift from reduced glutathione to oxidized glutathione in the presence of folate compared to the absence of folate (4% oxidized in the presence of folate versus 46% oxidized following two hours of folate deprivation). These data indicate that intracellular glutathione is being recruited to alleviate oxidative stress induced by the lack of folate. While no significant change in total glutathione levels were observed following brief (two hour) folate deprivation, HPLC analyses demonstrated that prolonged folate deprivation (e.g., for 24 hours) depleted total glutathione levels by approximately 45% (FIG. 4).

The effect of folate deprivation on the level of ROS was also examined. For monitoring of intracellular peroxide concentrations as an index of ROS, cultures received 10 µl/ml DFCD (2'7'-dichlorofluorescein diacetate; Kodak) for 20 minutes. Cultures were then visualized under fluorescein UV optics (perikaryon; Ekinci and Shea, 1999, supra).

Other neuronal cells and cell lines, can be used in this assay.

Figure 5:
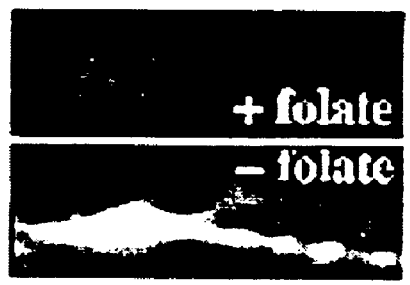
FIG. 5 is a pair of photomicrographs of cortical neurons grown in the presence or absence of folate, and in the presence of vitamin E and stained for reactive oxygen species (ROS) using dichloro-fluorescein diacetate (DFCD).
Figure 6:
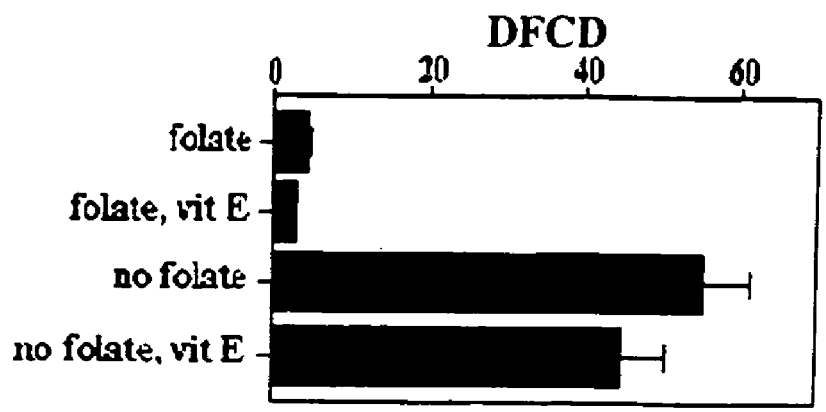
FIG. 6 is a bar graph that depicts the results of DFCD analysis for ROS in cortical neurons grown in the presence or absence of folate and in the presence or absence of vitamin E.

Folate deprivation for two hours also increased reactive oxygen species (ROS) in cultured cortical neurons (FIGS. 5 and 6). ROS generation during folate deprivation is not prevented by vitamin E (FIG. 6). In these experiments, cortical neurons were grown in folate-deficient medium for two hours in the presence or absence of 0.15 mg/ml vitamin E as alpha-tocopherol and assayed for ROS using DCFD as described in Example 2. However, in additional experiments it was observed that ROS induction by Abeta is prevented by vitamin E. Thus, ROS generation by folate deprivation is by a mechanism distinct from that involving the generation of ROS in the presence of Abeta.

Example 5

Folate Deficiency Induces Apoptosis

The question of whether folate deficiency is associated with apoptosis was investigated. Differentiated SH-SY-5Y cells were cultured without serum for 1-5 days in the presence and absence of folate and externalized phosphatidylserine (PS) was monitored (via meracyanine) as an index of apoptosis (Ekinci et al., 1999, supra). While similar levels of meracyanine fluorescence were observed after 1-3 days of folate deprivation, on day 5, folate-deprived cells displayed 77% more fluorescence that did cells receiving folate (Table 2). Overall detachment, a further sign of cell death, was evident by the seventh day in the serum-deprived cultures. The detachment phenomenon precluded longer experiments. These data indicate that folate deprivation induces apoptosis.

TABLE 2

Folate deprivation induces apoptosis

| Day of Culture | Mean ± SEM* | | Fold increase (−folate/+folate) |
|---|---|---|---|
| | +folate | −folate | |
| Day 1 | 34.0 ± 1.2 | 31.2 ± 1.4 | −8% |
| Day 3 | 40.9 ± 2.0 | 44.1 ± 4.1 | +8% |
| Day 5 | 63.7 ± 3.6 | 112.7 ± 5.7 | +77% |

*values represent arbitrary fluorescent units

Example 6

Folate Deficiency and Abeta Synergistically Increase ROS

Folate modulates intracellular glutathione in SH-SY-5Y cells (Example 3) and therefore regulates their capacity to buffer oxidative stress. Since Abeta is a key factor in the genesis of Alzheimer's disease, the impact of altering folic acid on Abeta neurotoxicity was also examined. In these experiments, cells were cultured in the presence and absence of 20 µM Abeta$_{25-35}$ for two hours.

Figure 7:
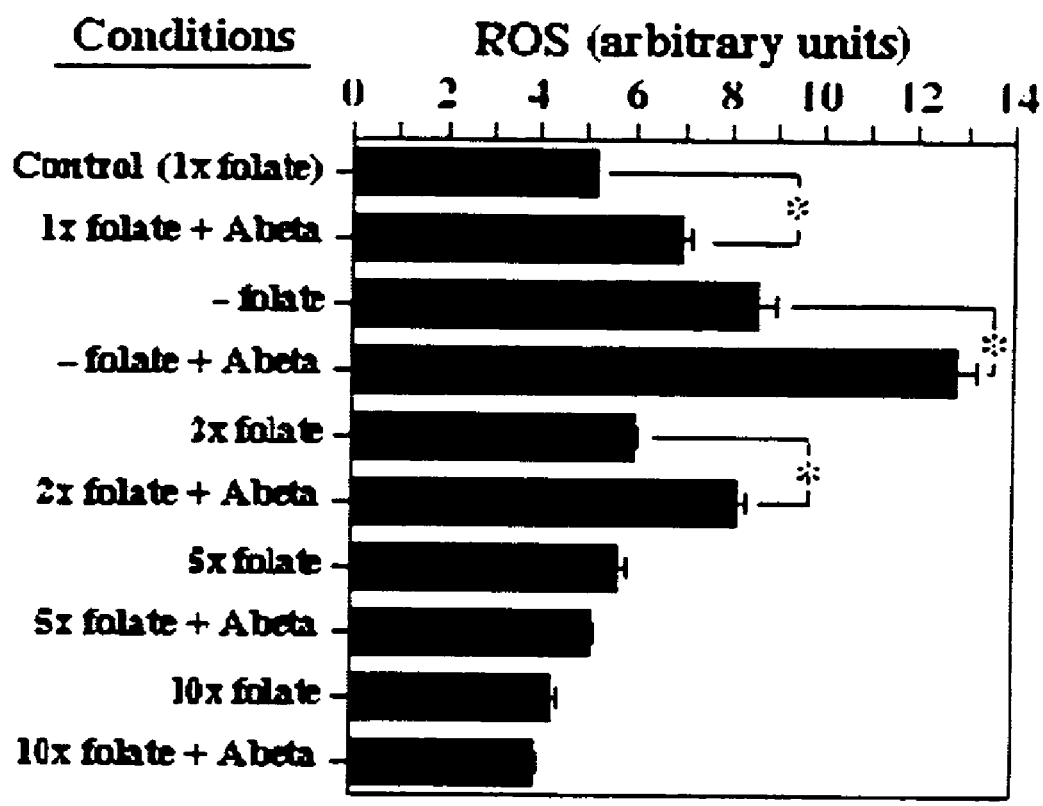
FIG. 7 is a bar graph showing the results of experiments in which differentiated SH-SY-5Y cells were cultured in DMEM (control), folate-free medium; or medium supplemented with folic acid at 2-10× the concentration present in DMEM, with or without 20 µM Abeta. ROS was then quantified using DFCD. Values represent mean±SEM from duplicate cultures from two separate experiments; asterisks denote statistical differences ±Abeta.

Folate deprivation induced a 64±5% increase in ROS in cells compared to cells cultured in the presence of folate. Abeta treatment in the presence of folate induced a 34±4% increase in ROS. However, Abeta treatment of folate-deprived cells induced a 144±10% increase in ROS (FIG. 7). If folate deprivation and Abeta had an additive effect on ROS, an increase of 98±9% would have been expected. The observed increase following Abeta treatment markedly exceeds this value, indicating that the combination of Abeta and folate deprivation exert a synergistic effect on ROS.

Example 7

Folate Supplementation Diminishes Abeta-induced ROS

The question of whether folate supplementation could abrogate the effects of Abeta on ROS was examined. Cultures were grown in DMEM, folate-free DMEM, or a medium supplemented with folic acid at 2-10 times the normal medium concentration in DMEM (4 mg/L), and each culture condition was assigned after growth in the presence or absence of 20 µM Abeta for two hours.

The Abeta-induced increase in ROS was prevented by 5×folate (20 mg/l). There was also a marginal decrease in ROS in otherwise untreated cells in the presence of 10×folate as compared to cells receiving 1-5×folate (FIG. 7).

These data show that dietary folic acid supplementation can be used to reduce neuropathology associated with AD.

Example 8

Effects of Folate Deficiency on Steady-State and Experimentally Induced Oxidative Stress in Normal and ApoE-Knockout Mice To determine whether data from cultured cells correlated with results in an in vivo system, the effects of folate and/or vitamin E deficiencies in normal and ApoE knockout mice (Jackson Laboratories, Bar Harbor, Me.) were examined. Specifically, the ability of mice to buffer steady-state oxidative species and to alleviate oxidative species induced in brain tissue following dietary challenge with iron as a pro-oxidant was examined.

Normal mice and homozygous ApoE−/− knockout mice (n=4 per diet regimen) received a basal diet (AIN-76; Purina; Shea and Rogers, 2002; Mol. Brain Res.; in press; Shea et al., 2002, Free Rad Biol Med J 33:276-282; Whittaker et al., 1996, Nutr. Cancer, 25:119-128) supplemented in some cases with iron (4 g/500 g total wet weight of AIN-76 basal diet mixture) as an oxidant in the presence and absence of folic acid (2 mg/500 g total diet weight) and vitamin E (provided as α-tocopherol oil; Sigma; 25 g/500 g total diet weight) for one month (diet and water ad libitum). After one month, total brain tissue was harvested and subjected to TBAR analyses as described in Wittaker et al. (1996, supra).

Figure 8:
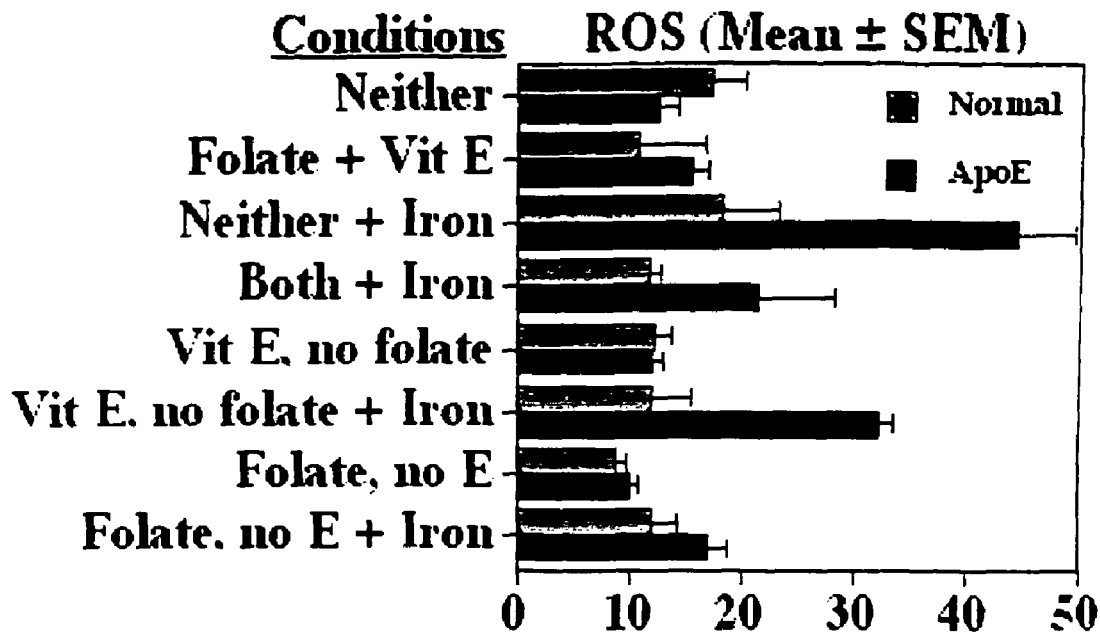
FIG. 8 is a bar graph showing the results of experiments in which ROS was assayed in central nervous system tissue (CNS) that was harvested from normal and Apo E–/– mice fed for one month with or without folate, vitamin E, and/or iron.

Consistent with the finding that folate deprivation depletes glutathione and generates ROS in cultured neurons, significant increases were observed in ROS values in the brains of mice whose diets were not supplemented with folate. Deficiencies in vitamin E alone did not increase ROS in iron-fed normal mice, but did increase ROS in ApoE−/− knockout mice. In normal mice, deficiencies in both folate and vitamin E did not cause a greater increase in ROS than did folate deprivation alone. However, deficiencies in folate and vitamin E did result in a further increase in ROS in ApoE knockout mice (FIG. 8).

These data confirm that ApoE knockout mice are less capable of buffering certain consequences of dietary oxidative stress than are normal mice, and that ROS can be altered in brain tissue in situ by dietary deficiencies and dietary challenge with pro-oxidants. Such effects can be monitored using the TBAR assay. These data also show that ApoE knockout mice are an appropriate model system for examining homocysteinemia. The ability of ApoE knockout mice to respond to oxidative challenge when provided with vitamin E and folate demonstrates that folate and vitamin E are effective agents for ameliorating the effects of Alzheimer's disease.

Example 9

ALCAR Reduces Abeta-Induced ROS and Apoptosis, and Prevents Abeta-Induced ATP Depletion The effect of ALCAR on differentiated SH-SY-5Y cells treated with Abeta was examined. Cells were cultured in 20 μM Abeta in the presence and absence of ALCAR. Some cultures were pretreated with 50 μM ALCAR for 30 minutes. In these experiments, the ALCAR-containing medium was replaced with medium containing Abeta and no ALCAR then incubated for two hours before being assayed. Cultures were assayed for ROS, apoptosis, and ATP.

Figure 9:
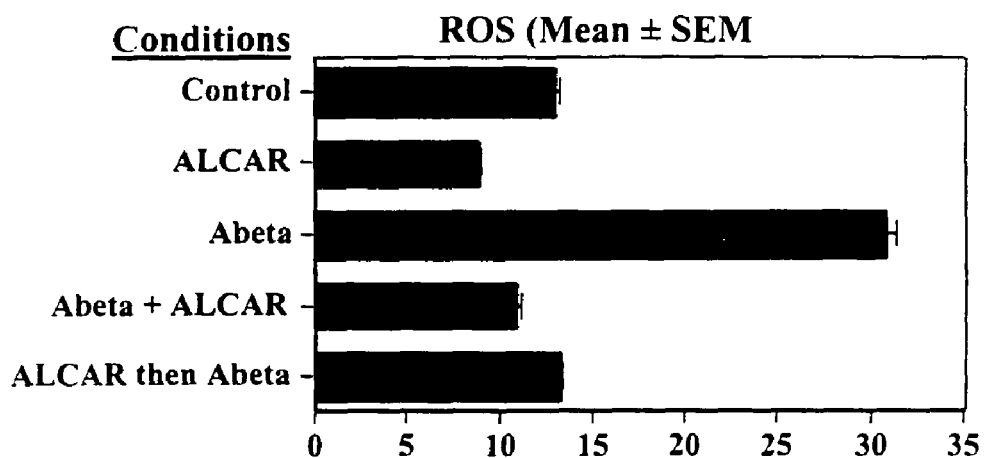
FIG. 9 is a bar graph showing the results of experiments examining apoptosis in which differentiated SH-SY-5Y cells were cultured in the presence or absence of Abeta, with or without ALCAR for two hours, and assayed for ROS using DCFD. In some experiments, cells were treated with ALCAR and then with medium containing Abeta without ALCAR (ALCAR then Abeta).
Figure 10:
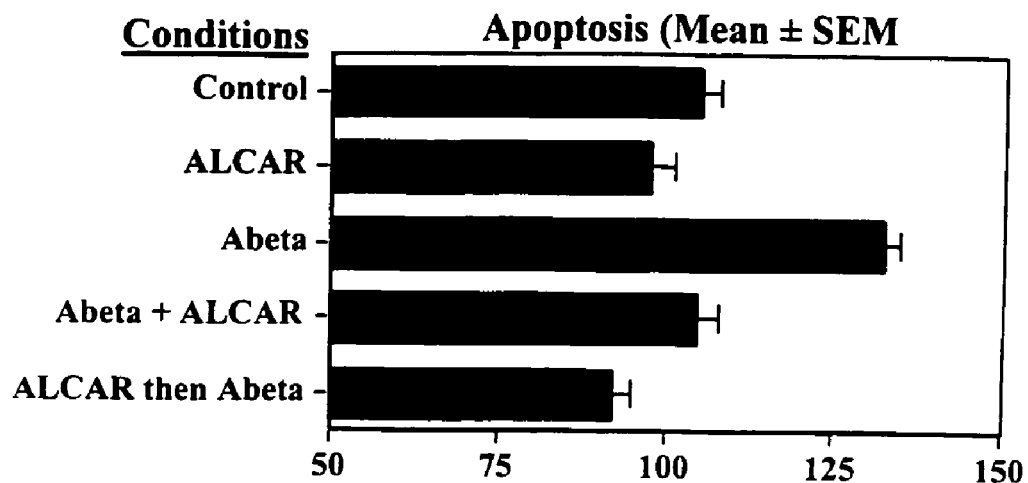
FIG. 10 is a bar graph showing the results of experiments examining apoptosis in which differentiated SH-SY-5Y cells cultured in the presence or absence of Abeta with or without ALCAR for two hours and assayed for externalized phosphatidyl serine (PS) using meracyanine fluorescence (the intensity of which is presented in arbitrary densitometric units). In some experiments, cells were treated with ALCAR and then with medium containing Abeta without ALCAR (ALCAR then Abeta).

Co-treatment of differentiated SH-SY-5Y cultures with 50 μM ALCAR reduced the effect of Abeta on ROS generation and on apoptosis. In addition, pretreatment with 50 μM ALCAR for 30 minutes, followed by its removal, was also effective at preventing Abeta neurotoxicity (FIGS. 9 and 10).

Figure 11:
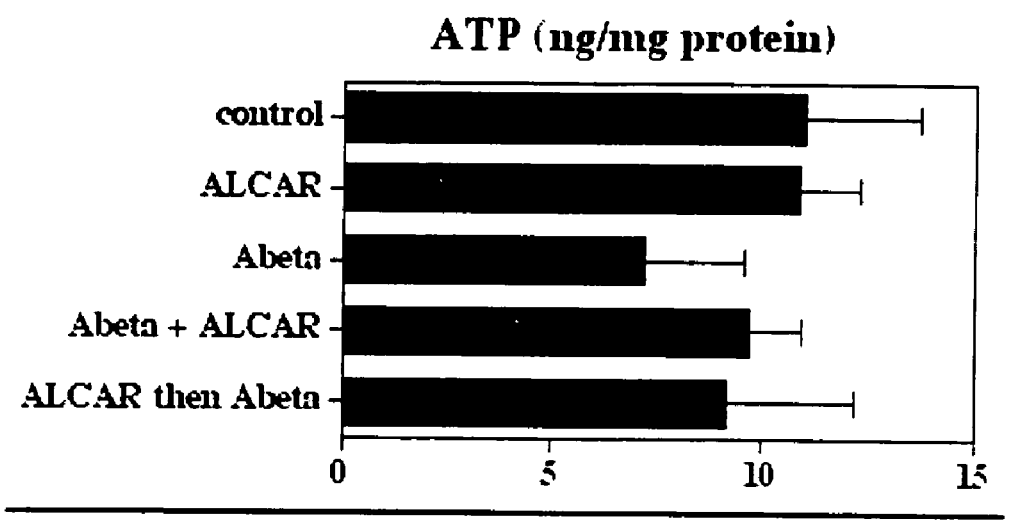
FIG. 11 is a bar graph showing the results of experiments examining apoptosis in which differentiated SH-SY-5Y cells cultured in the presence or absence of Abeta, with or without ALCAR for two hours, and assayed for ATP using spectrophotometric methods known in the art.

Since ALCAR is believed to act by maintaining ATP levels, ATP levels were examined in the presence and absence of ALCAR in cultures grown in the presence of Abeta. It was found that Abeta reduced cellular ATP. Such a depletion of energy reserves is consistent with induction of oxidative stress. Both co-treatment and prior treatment with 50 μM ALCAR prevented this reduction in ATP levels (FIG. 11).

These data show that ALCAR can contribute to alleviating effects associated with Alzheimer's disease.

Example 10

Activity of Combinations of Folate, Vitamin E, and ALCAR Against Abeta Toxicity It is shown herein that folate, vitamin E, and ALCAR can alleviate certain effects associated with neurotoxicity. The question was examined of whether combinations of these agents exhibited enhanced amelioration of Abeta toxicity (e.g., reduced ROS levels) compared to the effect of individual agents.

In these experiments, SH-SY-5Y cells were cultured as described above for two hours in the presence and absence of Abeta and concurrently exposed to various agents singly or in combination. Cells were then analyzed for ROS.

Figure 12:
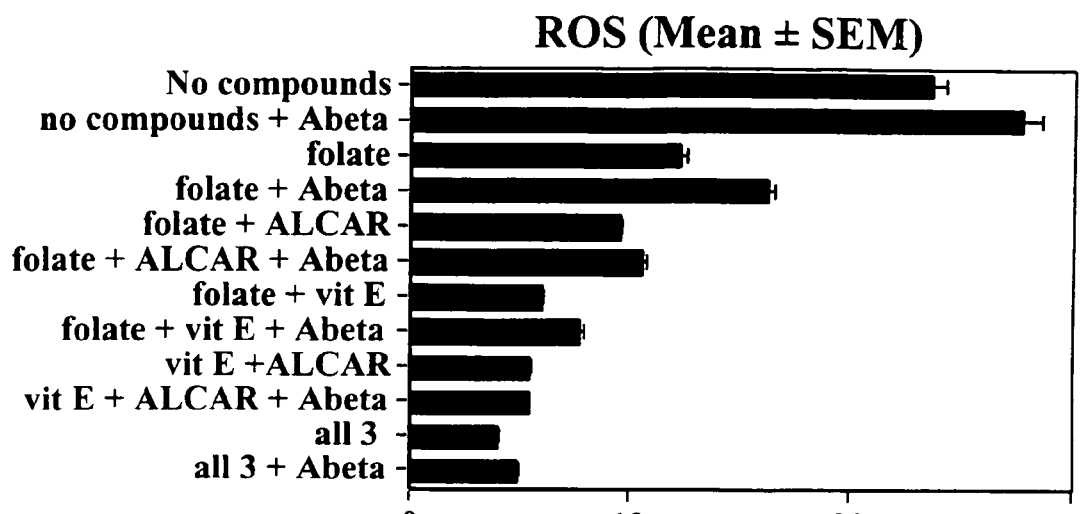
FIG. 12 is a bar graph showing the results of experiments examining ROS in differentiated SH-SY-5Y cultures grown in the presence or absence of Abeta with folate, ALCAR, and/or vitamin E.

Each of the three agents, folate, vitamin E, and ALCAR reduced ROS in control cells as well as in cells exposed to Abeta. Combinations of the agents were even more effective at reducing ROS (FIG. 12). These combinations include folate+ALCAR, folate+vitamin E, vitamin E+ALCAR, and vitamin E+ALCAR+folate. The combinations of agents were substantially more effective for reducing ROS than was folate alone. The treatments completely prevented any Abeta-induced increase in ROS above levels in control cells.

These data demonstrate the efficacy of nutriceutical formulations for diminishing ROS in cells. They also demonstrate the efficacy of the formulations for decreasing adverse effects associated with Abeta, e.g., in Alzheimer's disease. Thus, such formulations are useful for prevention and treatment of neurodegenerative diseases in which reactive oxygen species are produced as part of the pathologic process. Such diseases include Alzheimer's disease.

Example 11A

DZA Reduces the Impact of Folate Deprivation on ROS Generation

One likely major impact of folate deprivation appears to be homocysteine production (Fiskerstrand et al., 1997, J. Pharmacol. Exp. Ther. 282:1303-1311). To investigate this phenomenon, SY-SY-5Y cells were treated with 3-deaza-adenosine (DZA), which inhibits homocysteine formation by inhibition of S-adenosyl homocysteine hydrolase (Jeong et al., 1999, J. Biol. Chem., 274:18981-18988).

In these experiments, differentiated SH-SY-5Y cells were incubated in DMEM or DMEM lacking folate as described above. Test cultures also contained between 1 mM and 10 mM N-acetyl-L-cysteine (NAC). Incubations were for two hours. As in the experiments discussed supra, folate deprivation for two hours increased ROS by 38±4% when compared to cultures receiving folate. Inclusion of 25 μM DZA simultaneously with folate deprivation attenuated the increase in ROS by slightly more than half (Table 3). These data are the first demonstration that homocysteine formation is a contributing factor to oxidative stress resulting from folate deprivation.

These findings show that folate deprivation can be used to alter homocysteine production. Dietary folate supplementation can normally reduce homocysteine levels (Lucock et al., 1996, Biochem. Mol. Med. 59:104-111). The data also demonstrate that homocysteine production can be used as an assay for physiologic status with respect to oxidative stress and that compounds that reduce homocysteine are candidates for treating disorders such as Alzheimer's disease in which oxidative stress plays a role.

TABLE 3

DZA, an inhibitor of homocysteine formation, reduces ROS following folate deprivation

| Culture conditions | Mean ± SEM | % increase vs. control |
|---|---|---|
| folate (control) | 7.6 ± 0.3 | |
| no folate | 10.5 ± 0.5 | 38% |
| no folate + 25 µM DZA | 8.8 ± 0.3 | 16% |

Example 11B

The Glutathione Precursor, N-acetyl-L-cysteine (NAC), Protects against Folate Deprivation Glutathione is apparently not taken up directly by neurons (Schulz et al., 2000, Eur. J. Biochem., 267, 4904-4911). However, NAC, a glutathione precursor, protects both SH-SY-5Y cells and cultured cortical neurons from oxidative stress (Hatanaka et al., 1996, Biochem. Biophys. Res., Comm. 227: 513-518; Oliveri et al., 2001, J. Neurochem., 76:224-233), and increases intracellular glutathione (Ou et al., 1999, Neurotox., 20:793-804). It was not known whether NAC could modulate the effects of folate deprivation.

Figure 13:
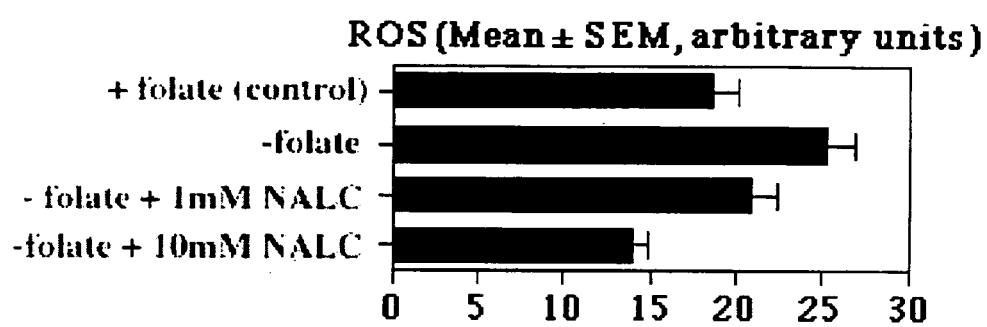
FIG. 13 is a bar graph showing the results of experiments examining ROS in differentiated SH-SY-5Y cultures grown in the presence of folate, in the absence of folate, or in the absence of folate with 1 mM NAC or 10 mM NAC.

To test the ability of NAC to attenuate the effects of folate deprivation, differentiated SH-SY-5Y cultures were treated for two hours with 1 mM or 10 mM NAC simultaneously with folate deprivation. ROS were then measured. Incubation with NAC prevented the increase in ROS that resulted from folate deprivation ($p<0.004$ for both 1 mM and 10 mM; FIG. 13).

These data show that NAC is a useful agent for treating neurodegenerative disorders in which there is oxidative stress associated with low levels or lowered accessibility to folate. In particular, NAC is useful for treating disorders associated with decreased levels of glutathione.

Example 12

NAC Decreases ROS in Cells Incubated in Abeta

Figure 14:
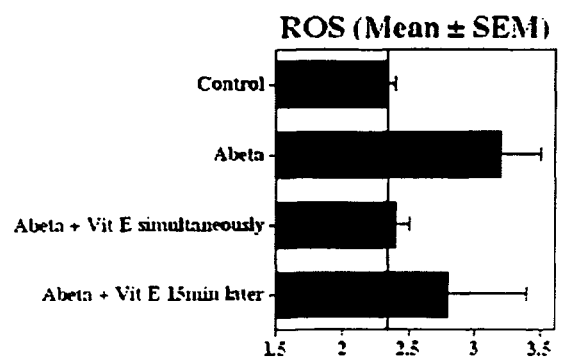
FIG. 14 is a bar graph showing the results of experiments examining ROS in differentiated SH-SY-5Y cultures grown in the presence or absence of Abeta and either pretreatment or simultaneous treatment with 0.15 mg/ml vitamin E.

As shown in FIG. 14, vitamin E is effective for reducing oxidative stress induced by Abeta in cultured cells if it is provided simultaneously with Abeta. In particular, ROS in cells cultured provided simultaneously with vitamin E and Abeta was approximately identical to that of control cells and substantially less than in cells incubated with Abeta alone.

However, if application of vitamin E was delayed as little as 15 minutes following application of Abeta, the efficacy of vitamin E was markedly reduced (FIG. 14 and Ekinci et al., 2000, Mol. Brain Res. 76:389-395). This is thought to be because vitamin E prevents membrane lipid peroxidation, but cannot curtail the downstream consequences of lipid peroxidation (Subraniam et al., 1998, Neurochem Res 23:1403-1410).

To investigate the efficacy of NAC for attenuating the generation of ROS after exposure to Abeta, SH-SY-5Y cultures were treated with Abeta as described supra. Vitamin E (0.15 mg/ml) or NAC (10 mM) was added to the cultures either simultaneously with Abeta or 15 minutes after addition of Abeta to the cultures (FIGS. 14 and 15).

Figure 15:
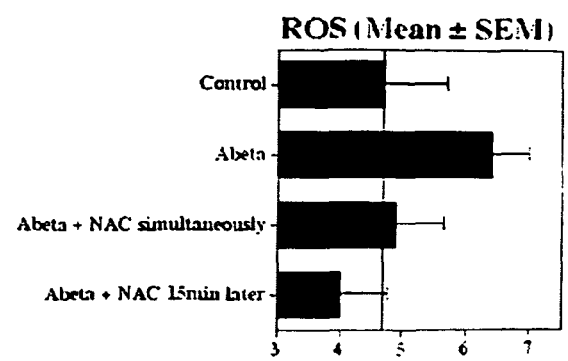
FIG. 15 is a bar graph showing the results of experiments examining ROS in differentiated SH-SY-5Y cultures grown in the presence or absence of Abeta and either pretreatment or simultaneous treatment with 10 mM NAC.

Analysis of ROS produced in these cultures after incubation for two hours under the various conditions demonstrated that NAC, but not vitamin E, quenched ROS when applied 15 minutes after addition of Abeta to the culture (FIGS. 14 and 15). This effect is likely to be due to increased generation of glutathione, which can quench ROS and free radicals that are formed secondarily to lipid peroxidation.

Example 13

SAM Inhibits Oxidative Stress Induced by Folate Deprivation

To test the effect of S-adenosyl-methionine (SAM) on the generation of ROS in response to folate deprivation, cultures were treated with or without folate for two hours as described supra. SAM (100 µM) was included in the test cultures and the presence of ROS was analyzed after the two hour incubation.

Figure 16:
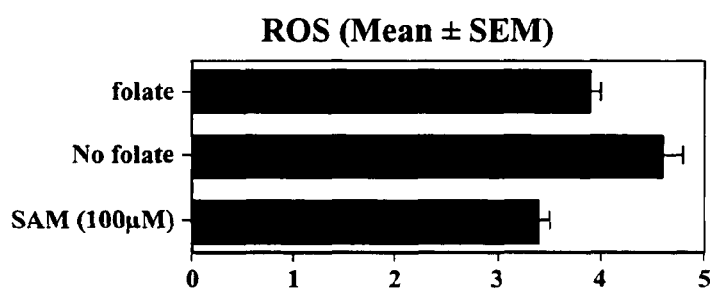
FIG. 16 is a bar graph showing the results of experiments examining ROS in differentiated SH-SY-5Y cultures grown in the presence or absence of folate. Folate-deprived cells were also treated with 100 µM SAM.

Cultures treated with SAM showed attenuation of the increase in ROS generated by folate deprivation (FIG. 16). In fact, SAM reduced ROS levels to a greater extent than did incubation of cells in the presence of folate. These data show that SAM is an effective agent for attenuating the production of ROS during folate deprivation and therefore is useful for treating neurodegenerative disorders involving generation of ROS, e.g., through pathways involving reduced folate.

Example 14

Combinatorial Neuroprotective Effects of DZA, NAC, and SAM

It is shown above that DZA, NAC, and SAM can alleviate certain effects associated with neurotoxicity. The question of whether combinations of these compounds exhibited additional effects was examined.

Differentiated SH-SY-5Y cultures were grown as described above (in the presence and absence of folate) and were treated with various combinations of DZA, NAC, and SAM using the concentrations described supra. After two hours in the various treatments, cultures were analyzed for the presence of ROS.

Figure 17:
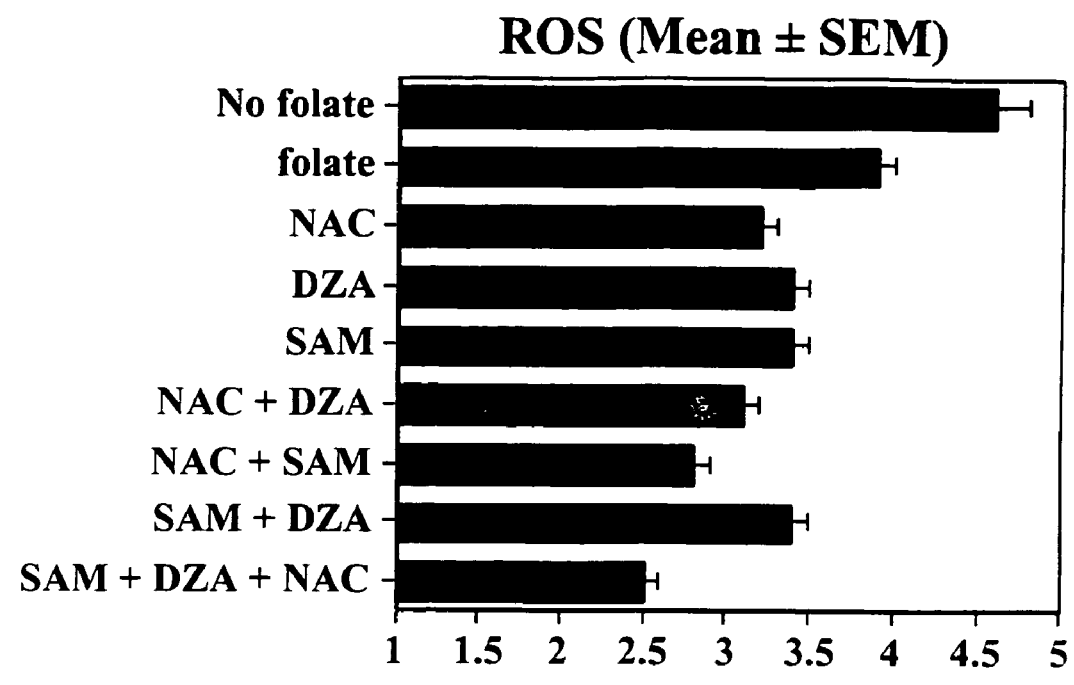
FIG. 17 is a bar graph showing the results of experiments examining ROS in differentiated SH-SY-5Y cultures grown in the presence or absence of folate, and in the presence or absence of 10 mM NAC, 25 mM DZA, and 100 µM SAM alone and in combinations.

As described above, all three agents were able to reduce ROS in folate-deprived cultures. Combined treatment with NALC+DZA or SAM+DZA, also reduced ROS in folate-deprived cultures. Combined treatment with SAM and NAC reduced ROS more than any of the agents alone or the combinations of NALC+DZA or SAM+DZA (FIG. 17). Treatment with DZA+NALC+SAM provided the maximal decrease in ROS. Even in the absence of folate, these agents reduced ROS to levels markedly below those detected in the presence of folate. The beneficial effects of these agents include cellular antioxidant protection, generation of intracellular glutathione, diminished production of homocysteine, and maintenance of DNA methylation. Some agents appear to provide their effects in different ways, thus combinations of agents provide broader protection against various pathways that generate ROS.

These data demonstrate the advantageous effects of combinations of agents and show that such combinations can provide effective treatments for disorders involving the generation of ROS, particularly neurodegenerative disorders such as Alzheimer's disease.

Example 15

Compensation for Folate Deficiency by NAC, DZA, AND SAM in Neuronal Cultures The effects of NAC, DZA, and SAM individually and in combination on oxidative damage, homocysteine levels, and glutathione levels was investigated.

Supplementation with NAC Increases Intracellular Cysteine and Glutathione in Neuronal Cultures NAC directly scavenges ROS and also provide a source of intracellular cysteine for synthesis of glutathione during conditions of oxidative stress. Experiments were conducted to determine whether NAC mediates its protective effects following folate deprivation in part via increasing total glutathione. Differentiated SH-SY-5Y cells with and without NAC treatment were subjected to HPLC along with 50 µM each of multiple thiol standards ("Standards") as indicated in FIGS. 18A to 18C.

A marked increase in cysteine and glutathione was observed following NAC treatment in the absence of folate. A small initial peak is seen in the traces in all samples (retention time of approximately one minute) and indicates the "front" of the sample.

These data demonstrate the ability to monitor the presence of various thiols by HPLC. They also confirm the efficacy of NAC addition for increasing levels of the endogenous antioxidant glutathione. These data further support the use of NAC in vivo as an effective treatment for alleviating neurologic symptoms associated with ROS, and are likely to contribute to the ability of NAC to buffer the extent of ROS generated following folate deprivation.

Effect of DZA on Homocysteine Formation and Neurotoxicity from Folate Deprivation To examine the effects of DZA on deleterious effects related to folate deprivation, first, homocysteine production was measured in cell lysates of SH-SY-5Y cells using HPLC. In these experiments, differentiated SH-SY-5Y cells were cultured for two hours in the presence or absence of folate. Medium was then decanted, cells were scraped from the plate and homogenized, and medium and cellular lysates, along with an aliquot of fresh medium that had not been in contact with cells, were subjected to HPLC analyses.

In accord with prior studies demonstrating that homocysteine is either rapidly metabolized or exported, and that increased homocysteine formation increases its export rather than intracellular accumulation, homocysteine levels were undetectable (<1 nM) within cell lysates both before and after folate deprivation. Homocysteine was not detectable in fresh medium. Homocysteine levels in medium of cells cultured for two hours in the absence of folate increased ten-fold to approximately 300 nM. Levels of homocysteine in medium from cells cultured for two hours in the presence of folate was about 30 nM (FIG. 19).

Differentiated SY-SY-5Y cells were also treated with 3-deaza-adenosine (DZA), which inhibits homocysteine formation, when provided to cells simultaneously undergoing folate deprivation. Inclusion of 25 µM DZA during folate deprivation prevented HCY formation and export to a level below that observed in cultures receiving folate, and so attenuated the increase in ROS by approximately 50% (FIG. 19).

Effect of SAM on HC-induced Apoptosis

Figure 20:
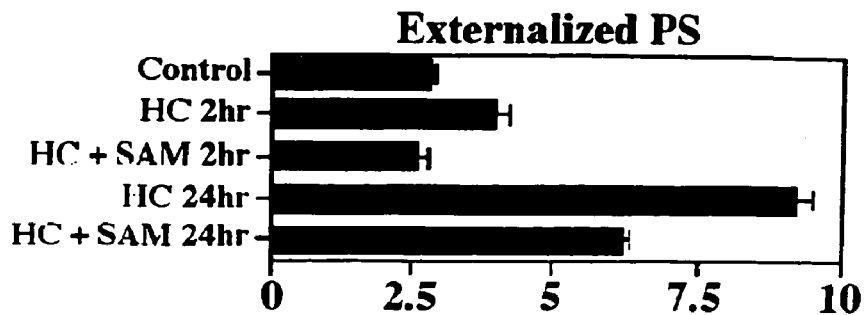
FIG. 20 is a bar graph that depicts the results of experiments in which cortical neurons were treated with 250 µM homocysteine with or without 100 µM SAM, after which cultures were monitored for externalized PS via meracyanine staining as an indication of apoptosis. Values represent the mean (±standard error of the mean) in arbitrary densitometric units derived from densitometric analyses of 10-50 neurons from two cultures under each condition from two separate independent experiments.

Homocysteine induces apoptosis in cultured cells. To investigate the effect of SAM on HC-induced apoptosis, 100 µM SAM and homocysteine were added to cultured SH-SY-5Y cells and apoptosis was monitored by meracyanine staining to detect the externalization of PS. Homocysteine progressively induced externalization of PS (FIG. 20); values for HC-treated cultures differed statistically from untreated controls at 2 and 24 hours (p<0.001, one-way ANOVA), indicating a progressive increase in apoptosis. SAM prevented PS externalization at 2 hours and reduced it by approximately 50% at 24 hours (p<0.05, one-way ANOVA with Fisher's PLSD).

These data are consistent with the possibility that impaired transmethylation of DNA plays a role in HC-mediated apoptosis, but do not exclude the possibility that other critical transmethylation events are involved in induction of neuronal apoptosis by HC. In addition, inhibition of DNA damage did not attenuate the increase in cytosolic calcium resulting from homocysteine treatment, underscoring the multifactoral neurodegenerative impact of HC; that is, homocysteine can induce neurodegeneration both by DNA damage and by calcium-induced excitotoxicity. These data demonstrate that treatment with multiple agents is desirable to attenuate the neurotoxicity of folate deprivation and resultant homocysteine formation.

Example 16

Efficacy of Combined Treatment with DZA, NAC and SAM in Normal and ApoE−/− mice To determine the effect of combined treatment with DZA, NAC, and SAM in a mouse model of Alzheimer's disease (ApoE−/− mice), oxidative damage in such animals was examined following folate deprivation. In these experiments, normal and ApoE−/− mice were treated for one month with the complete diet discussed above (containing folate and vitamin E and lacking the iron challenge) or with a "deficient diet" (the basal diet lacking folate and vitamin E and containing high dietary iron as a pro-oxidant; Shea and Rogers, 2002, Mol. Brain Res. 108:1-6). Additional mice received the deficient diet supplemented with DZA (0.4 g/kg total diet weight), SAM (80 mg/kg diet weight) and NAC (1 g/kg diet weight). Total brain tissue was harvested and analyzed for TBARs.

Figures 21A, 21B:
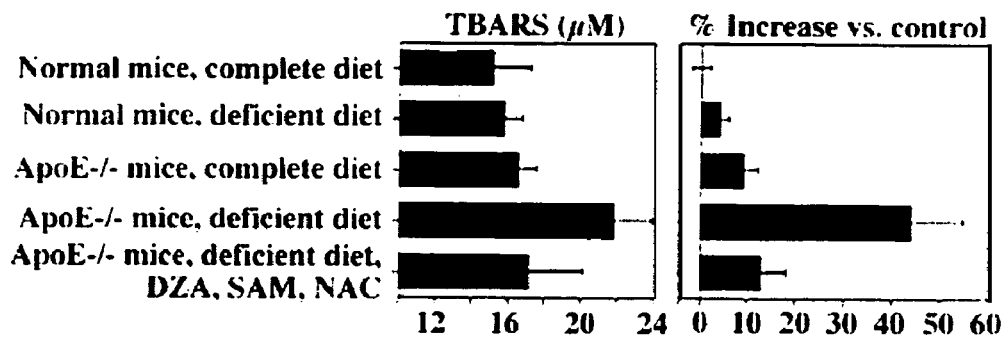
FIGS. 21A and 21B are a pair of bar graphs that depict the results of experiments in which oxidative damage was measured in brain extracts of normal and ApoE−/− mice receiving a diet for one month lacking iron or folic acid. TBAR values were measured. Values in the graph of FIG. 21A represent mean±SEM μmol TBARs/mg total protein, and FIG. 21B show the mean±SEM increase versus controls with control defined as normal mice receiving the complete diet) as compiled from two independent experiments, with n=2-3 mice for each diet per experiment. "Complete diet" is defined as the basal diet (above) supplemented with folate and vitamin E and lacking iron. "Deficient diet" is the basal diet lacking folate and vitamin E and containing iron (e.g.

Analysis of brain tissue showed that combined treatment with DZA, NAC, and SAM decreased brain oxidative damage in ApoE−/− mice following folate deprivation (FIGS. 21A and 21B). In particular, TBAR scores for normal mice fed a folate-deficient diet was about less than 10% higher than controls while ApoE−/− mice fed a complete diet had a TBAR score about 10% higher than controls. However, when ApoE−/− mice were fed a folate-deficient diet, the TBAR was nearly 50% higher than controls. This effect was reduced to slightly more than 10% higher than controls in folate-deprived ApoE−/− mice whose diet was supplemented with DZA, NAX, and SAM. These studies confirm the efficacy of DZA, NAC, and SAM in situ.

Example 17

Effect of Combined Treatment with DZA, NAC, and SAM on Homocysteine Accumulation and Glutathione As discussed herein, folate deprivation results in accumulation of homocysteine and a compensatory increase in glutathione. Experiments were conducted evaluating the effects of combined treatment with DZA, NAC, and SAM on these phenomena.

Normal and ApoE−/− mice received the complete and deficient diets (as described supra) for one month, after which plasma was harvested and analyzed by HPLC for homocysteine and glutathione. Aliquots (100 µl) of plasma from the normal and ApoE−/− mice were subjected to HPLC analyses. There was an increase in HC, and the compensatory increase in glutathione (Shea et al., 2002, supra) following folate deprivation coupled with dietary iron challenge ("deficient diet"). Further, inclusion of DZA, SAM, and NAC at the same concentrations discussed above prevented these increases ($p \leq 0.03$; Student's t test). Data are derived from 2-3 mice each from 2 independent experiments.

Figures 22A, 22B:
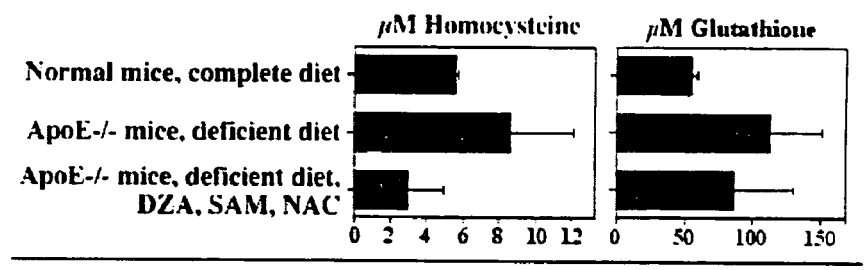
FIGS. 22A and 22B are a pair of bar graphs that depict the results of experiments in which homocysteine (22A) and glutathione (22B) levels were assayed in normal and ApoE−/− mice whose diets were supplemented with DZA, NAC, and SAM as described herein. Aliquots (100 μl) of plasma from the normal and ApoE−/− mice described were subjected to HPLC analyses as described herein.

As described previously (Shea and Rogers, 2002, Mol. Brain Res., 108:1-6; Shea et al., 2002, Free Rad. Biol. Med., 33:1115-1120), folate deprivation combined with dietary iron challenge increased homocysteine levels, and induced a compensatory increase in glutathione in ApoE−/− mice (see, FIG. 22B). The data provided herein demonstrate that combined treatment with DZA, NAC, and SAM prevented both of these increases (FIGS. 22A and B). These data demonstrate the ability of DZA, NAC, and SAM to prevent homocysteine formation despite folate deficiency, as well as alleviate compensatory glutathione production.

Example 18

Effect of DZA, NAC, and SAM Treatment on Glutathione Synthase During Folate Deficiency and Iron Challenge Experiments were performed to determine whether the compensatory increase in glutathione resulting from folate deprivation and iron challenge of ApoE−/− mice (Shea et al., 2002b), and its alleviation by combined treatment with DZA, NAC, and SAM (see FIG. 22) were derived in part from changes in transcription of glutathione synthase. To accomplish this, total mRNA was extracted as described previously (Tchantchou, 2001, Master's thesis, VRIJE Universiteit Brussel, Brussels, Belgium) from freshly-harvested brain tissue from normal and ApoE−/− mice that were maintained on normal or folate-deficient dietary regimes described above. These cortical samples of mRNA were subjected to RT-PCR using standard short-fragment primers corresponding to glutathione synthase (GS) (product size 88 bp) using methods known in the art, with 20 pmol of short-ligand primers for glutathione synthase. Only the relevant portion of the gel is shown in FIG. 23A. The accompanying graph in FIG. 23B depicts densitometric analyses (mean±st dev) of the anticipated 88 bp band from three mice for each diet. The RT-PCR product from a single representative mouse under each dietary regimen is presented in the gel.

An increased signal indicating an increase in glutathione synthase transcription was observed in ApoE−/− mice maintained on the deficient diet. Moreover, supplementation of this diet with DZA, NAC, and SAM alleviated the increase in glutathione synthase transcription. These data suggest that increased transcription of glutathione synthase contributes to the observed compensatory increase in glutathione. Increased transcription of glutathione synthase to compensate for ApoE−/− deficiency supports the hypothesis that altered gene transcription may be invoked to compensate for genetic predisposition to neurodegeneration. A p value of <0.006 was obtained for ApoE−/− mice on the deficient diet versus normal mice on the complete diet (Student's t test), with $p \geq 0.3$ for all other values vs. normal mice on the complete diet.

Example 19

Effects of Folate Deficiency and Iron Challenge on Cognitive Performance and Treatment with DZA, NAC, and SAM The effects of a deficient diet on memory were examined using normal and ApoE−/− mice. The mice were maintained on diets described herein (n=6/diet) for one month, then subjected to the classical Y maze test. The pattern of exploration of the Y maze was recorded over five minute intervals for each mouse, with the cage cleaned and dried between tests to avoid influence of the prior mouse on subsequent exploration. Under normal conditions, mice will successively alternate explorations among the three arms of the maze; i.e., a mouse leaving the left arm and exploring the top arm should next enter the right arm rather than first returning to the left arm. The frequency in which mice visited each of the three arms during any three-arm visitation sequence versus the total visitations defines the "% alternation."

ApoE−/− mice maintained on the deficient diet for one month exhibited a degree of impaired performance ($p<0.09$; ANOVA, Fischer's PLSD, all other values statistically identical) compared to normal mice maintained on either diet or ApoE−/− mice maintained on the complete diet; i.e., they failed to alternate arms of the maze and instead re-explored the arm from which they had last exited (FIG. 24). By contrast, supplementation of the deficient diet with DZA, NAC, and SAM restored normal exploratory behavior to ApoE−/− mice. These data were derived from two independent experiments with n=3 mice per diet for each experiment (total n=6 mice for each group, with mixed males and females).

Consideration was given to whether gender differences contributed to the impact of the above dietary regimens. Independent analyses of the data obtained for males and females revealed that the above differences were attributable entirely to males and not females. In our preliminary studies, male ApoE−/− mice maintained on the deficient diet differed statistically from normal mice maintained on the complete diet ($p<0.047$), while all other groups were statistically identical ($p>0.10$) to normal mice maintained on the complete diet. In contrast to males, no statistical difference was detected among any of the various diets for female mice (ANOVA, Fischer's PLSD). These data indicate that the combined deleterious influences of genetic predisposition to oxidative stress (the ApoE−/− genotype), dietary deficiencies (lack of folate and vitamin E), and environmentally-induced oxidative stress (dietary iron challenge) resulted in memory impairment as evidenced by diminished performance in the Y-maze test. They further indicate that supplementation with DZA, NAC, and SAM alleviated this impairment in performance.

The mice from the T maze experiments were subsequently sacrificed to generate the data on oxidative damage and plasma homocysteine and glutathione presented above. Accordingly, the impact of the dietary regimens and supplements was assayed on the combined parameters of oxidative damage, HC, endogenous antioxidants, and memory impairment in the same mice.

Figure 25:
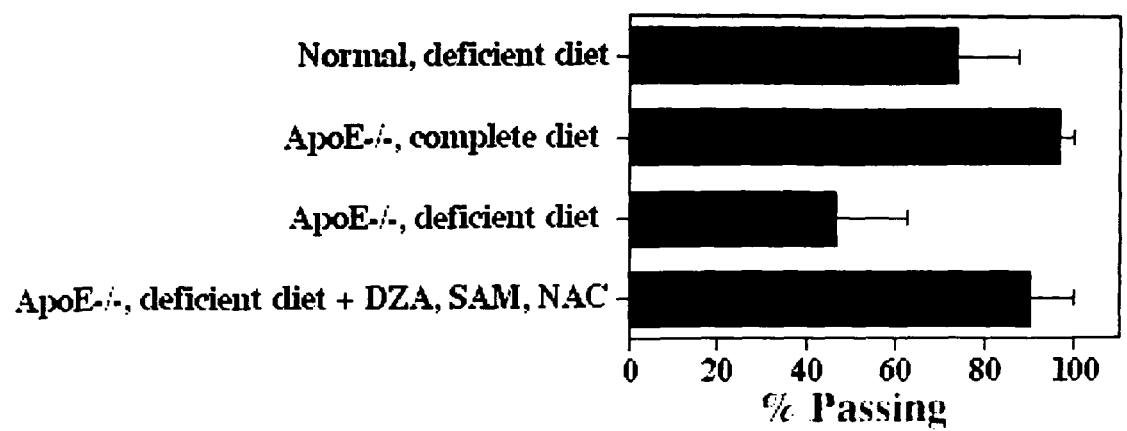
FIG. 25 is a bar graph depicting the results of experiments in which normal and ApoE−/− mice that had been subjected to various dietary regimens were tested in a Y maze reward-based test.

The impact of the model developed for inducing cognitive deficiencies using folate deprivation and iron challenge was also examined using the traditional "T maze" reward-based system. In these experiments, mice were placed at the bottom of a T-shaped maze, with one arm of the maze blocked. Therefore, mice could explore only one arm of the maze. Each arm of the maze contained a depression containing a small amount of sweetened milk. Mice were allowed to locate and consume the milk in the available arm, were then returned to the bottom of the maze, and the block was removed from the other arm. If the mouse entered the opposite (newly-unblocked arm), it was scored as passing; if it instead re-explored the previously-visited arm (from which the reward had already been consumed), it was scored as failing. The rationale for these criteria are similar to the alternation described above for the Y maze; given a choice, mice under normal conditions will demonstrate a greater tendency to explore a novel area rather than re-explore previously-visited territory. Mice were tested in the maze three times, and the percentage of passing trials calculated for each mouse. ApoE−/− mice that had received the deficient diet displayed significantly reduced cognitive performance in this single trial ($p \leq 0.005$ vs. normal and ApoE−/− mice receiving a complete diet), although normal mice on the deficient diet demonstrated a trend towards significant reduction ($p \leq 0.13$ vs. normal mice receiving a complete diet). Supplementation with DZA, SAM, and NAC alleviated this impairment in ApoE−/− mice ($p \leq 0.57$ vs. normal mice receiving a complete diet; FIG. 25).

The experiments described herein also demonstrate that a combination of ApoE−/− phenotype and dietary deficiency in mice provides a model for cognitive impairment and thus a model for testing compounds that are candidates for reducing cognitive impairments in humans (e.g., disorders resulting from folate deficiency such as impaired folate metabolism and Alzheimer's disease). The Examples provided herein indicate that folate deficiency severely compromises the ability of ApoE−/− mice to withstand oxidative stress as quantified by overall oxidative damage, depletion of endogenous antioxidant capacity (despite compensatory increased glutathione), increased plasma HC, and cognitive performance. Moreover, combined treatment with DZA, NAC, and SAM improved these parameters.

Cell culture data suggest that DZA is effective at inhibition of homocysteine production, SAM prevents DNA damage, and that NAC increases glutathione, thus, a combination of these compounds provides a more complete treatment for treating disorders resulting from a combination of effects than treatment with only one of these compounds.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising 3-deaza-adenosine (DZA), N-acetyl-L-cysteine (NAC), and S-adenosylmethionine (SAM) in combination or in individual dosage forms, wherein a unit dose of the composition reduces a level of reactive oxygen species (ROS) in an in vitro neural cell culture.

2. The composition of claim 1, further comprising at least one of folate, acetyl-L-carnitine (ALCAR), and vitamin E.

3. The composition of claim 1, further comprising at least two of folate, acetyl-L-carnitine (ALCAR), and vitamin E.

4. The composition of claim 1, further comprising folate, acetyl-L-carnitine (ALCAR), and vitamin E.

5. The composition of claim 4, wherein the composition comprises about 200-2000 μg folate, about 50-3000 I.U. vitamin E, and about 200-4000 mg acetyl-L-carnitine (ALCAR).

6. The composition of claim 2, wherein the composition comprises N-acetyl-L-cysteine (NAC), S-adenosylmethionine (SAM), 3-deaza-adenosine (DZA), and folate.

7. The composition of claim 2, wherein the composition comprises N-acetyl-L-cysteine (NAC), S-adenosylmethionine (SAM), 3-deaza-adenosine (DZA), and acetyl-L-carnitine (ALCAR).

8. The composition of claim 2, wherein the composition comprises N-acetyl-L-cysteine (NAC), S-adenosylmethionine (SAM), 3-deaza-adenosine (DZA), and vitamin E.

9. The composition of claim 3, wherein the composition comprises N-acetyl-L-cysteine (NAC), S-adenosylmethionine (SAM), 3-deaza-adenosine (DZA), folate, and acetyl-L-carnitine (ALCAR).

10. The composition of claim 3, wherein the composition comprises N-acetyl-L-cysteine (NAC), S-adenosylmethionine (SAM), 3-deaza-adenosine (DZA), folate, and vitamin E.

11. The composition of claim 3, wherein the composition comprises N-acetyl-L-cysteine (NAC), S-adenosylmethionine (SAM), 3-deaza-adenosine (DZA), acetyl-L-carnitine (ALCAR), and vitamin E.

* * * * *